US012287231B2

(12) United States Patent
Irlam et al.

(10) Patent No.: US 12,287,231 B2
(45) Date of Patent: Apr. 29, 2025

(54) MEASUREMENT SYSTEM

(71) Applicant: Chiaro Technology Limited, London (GB)

(72) Inventors: Christopher James Irlam, London (GB); Jeremy William Crouch, London (GB); Thomas Michael Malloy, London (GB); Brian McVeigh, London (GB); Jonathan James Harvey Heffer, London (GB); Benjamin Peter Pescud, London (GB); Jack Cyril Biltcliffe, London (GB); Macdara O'Shea, London (GB); Daniel John Thompson, London (GB)

(73) Assignee: Chiaro Technology Limited, London (GB)

( * ) Notice: Subject to any disclaimer, the term of this patent is extended or adjusted under 35 U.S.C. 154(b) by 0 days.

(21) Appl. No.: 18/418,116

(22) Filed: Jan. 19, 2024

(65) Prior Publication Data
US 2024/0210230 A1 Jun. 27, 2024

Related U.S. Application Data

(63) Continuation of application No. 18/445,457, filed on Aug. 31, 2023.

(30) Foreign Application Priority Data

Aug. 31, 2022 (GB) .................................... 2212673

(51) Int. Cl.
G01F 22/00 (2006.01)
A61M 1/06 (2006.01)
(52) U.S. Cl.
CPC ............. *G01F 22/00* (2013.01); *A61M 1/069* (2021.05)

(58) Field of Classification Search
CPC ................................ G01F 22/00; A61M 1/069
See application file for complete search history.

(56) References Cited

U.S. PATENT DOCUMENTS

| 11,135 A | 6/1854 | Needham |
| 949,414 A | 2/1910 | Cunningham |

(Continued)

FOREIGN PATENT DOCUMENTS

| CN | 2452494 Y | 10/2001 |
| CN | 1799436 A | 7/2006 |

(Continued)

OTHER PUBLICATIONS

4MD Medical, "Assembling Spctra Breast Pump Parts," YouTube [online], dated Nov. 13, 2016, URL: http:// www.youtube.com/ watch?v=ChV8xQfcBxU, 3 pages.

(Continued)

*Primary Examiner* — Tarun Sinha
(74) *Attorney, Agent, or Firm* — Sterne, Kessler, Goldstein & Fox P.L.L.C.

(57) ABSTRACT

There is provided a method of measuring liquid volume in a sealed container of a breast pump of known volume comprising liquid and gas. The method includes a measurement phase, measuring the volume of gas in the container by changing a first parameter of the gas by a known amount. The method also includes measuring a change in a second parameter of the gas; calculating the volume of gas in the container using the measured change and a predetermined operation equation; and determining the volume of liquid in the container based on the calculation.

30 Claims, 16 Drawing Sheets

(56) References Cited

U.S. PATENT DOCUMENTS

| | | |
|---|---|---|
| 2,849,881 A | 9/1958 | Anderson |
| 3,840,012 A | 10/1974 | Rushton, Jr. |
| 4,263,912 A | 4/1981 | Adams |
| 4,270,538 A | 6/1981 | Murphy |
| 4,390,024 A | 6/1983 | Williams |
| 4,535,627 A | 8/1985 | Prost et al. |
| 4,673,388 A | 6/1987 | Schlensog et al. |
| 4,772,262 A | 9/1988 | Grant et al. |
| 4,857,051 A | 8/1989 | Larsson |
| 4,929,229 A | 5/1990 | Larsson |
| 5,406,063 A | 4/1995 | Jelen |
| 5,474,683 A | 12/1995 | Bryant et al. |
| 5,514,166 A | 5/1996 | Silver et al. |
| 5,542,921 A | 8/1996 | Meyers et al. |
| 5,571,084 A | 11/1996 | Palmer |
| 5,941,847 A | 8/1999 | Huber et al. |
| 5,954,690 A | 9/1999 | Larsson |
| 5,973,770 A | 10/1999 | Carter et al. |
| 6,045,529 A | 4/2000 | Nuesch |
| 6,090,065 A | 7/2000 | Giles |
| 6,227,936 B1 | 5/2001 | Mendoza |
| 6,257,070 B1 * | 7/2001 | Giallorenzo ............ G01F 15/08 |
| | | 73/861.04 |
| 6,328,709 B1 | 12/2001 | Hung et al. |
| 6,358,226 B1 | 3/2002 | Ryan |
| 6,379,327 B2 | 4/2002 | Lundy |
| 6,383,163 B1 | 5/2002 | Kelly et al. |
| 6,440,100 B1 | 8/2002 | Prentiss et al. |
| 6,461,324 B1 | 10/2002 | Schlensog |
| 6,547,756 B1 | 4/2003 | Greter et al. |
| 6,579,258 B1 | 6/2003 | Atkin et al. |
| 6,652,484 B1 | 11/2003 | Hunckler et al. |
| 6,663,587 B2 | 12/2003 | Silver et al. |
| 6,673,036 B1 | 1/2004 | Britto |
| 6,749,582 B2 | 6/2004 | Britto et al. |
| 6,840,918 B1 | 1/2005 | Britto et al. |
| 6,887,210 B2 | 5/2005 | Quay |
| 7,048,519 B2 | 5/2006 | Fong et al. |
| 7,201,735 B2 | 4/2007 | Atkin et al. |
| 7,223,255 B2 | 5/2007 | Myers et al. |
| D548,831 S | 8/2007 | Charlez |
| 7,312,554 B2 | 12/2007 | Vogeley |
| 7,314,400 B2 | 1/2008 | Fildan et al. |
| 7,347,089 B1 * | 3/2008 | Kelley .................... G01F 25/20 |
| | | 73/149 |
| 7,559,915 B2 | 7/2009 | Dao et al. |
| 7,641,629 B2 | 1/2010 | Yuen |
| 7,662,018 B1 | 2/2010 | Thompson |
| 7,666,162 B2 | 2/2010 | Renz et al. |
| 7,776,008 B2 | 8/2010 | Renz et al. |
| 7,833,190 B1 | 11/2010 | Hall |
| 7,875,000 B2 | 1/2011 | Krebs et al. |
| 8,057,425 B1 | 11/2011 | Myers et al. |
| 8,118,772 B2 | 2/2012 | Dao et al. |
| 8,187,227 B2 | 5/2012 | Luzbetak et al. |
| 8,216,179 B2 | 7/2012 | Bosshard et al. |
| 8,262,606 B2 | 9/2012 | Greter et al. |
| 8,282,596 B2 | 10/2012 | Greter et al. |
| 8,376,986 B2 | 2/2013 | Van Schijndel et al. |
| 8,608,685 B2 | 12/2013 | Tashiro et al. |
| 8,702,646 B2 | 4/2014 | Garbez et al. |
| 8,801,495 B1 | 8/2014 | Guindon |
| 8,876,760 B2 | 11/2014 | Bosman et al. |
| 8,926,556 B2 | 1/2015 | Van Eijkelenborg et al. |
| 9,033,913 B2 | 5/2015 | Khalil et al. |
| 9,173,587 B2 | 11/2015 | Van Schijndel et al. |
| 9,345,274 B1 | 5/2016 | Prill |
| 9,498,565 B2 | 11/2016 | Nowroozi et al. |
| 9,539,377 B2 | 1/2017 | Makower et al. |
| 9,580,863 B2 | 2/2017 | Bader et al. |
| D788,293 S | 5/2017 | Eckstein et al. |
| D809,646 S | 2/2018 | Mason et al. |
| 9,919,084 B2 | 3/2018 | Pollen et al. |
| 10,039,871 B2 | 8/2018 | Pollen et al. |
| 10,046,097 B2 | 8/2018 | Thompson et al. |
| D832,995 S | 11/2018 | Mason et al. |
| 10,149,929 B2 | 12/2018 | Furrer et al. |
| 10,195,321 B2 | 2/2019 | Tatterfield et al. |
| 10,335,525 B2 | 7/2019 | Felber et al. |
| 10,398,816 B2 | 9/2019 | Chang et al. |
| 10,625,005 B2 | 4/2020 | Chang et al. |
| 10,660,995 B2 | 5/2020 | Makower et al. |
| D888,225 S | 6/2020 | Askem et al. |
| 10,864,306 B2 | 12/2020 | Fujisaki |
| 10,881,766 B2 | 1/2021 | O'Toole et al. |
| 10,926,011 B2 | 2/2021 | O'Toole et al. |
| 10,987,455 B2 | 4/2021 | Aalders et al. |
| 11,260,151 B2 | 3/2022 | O'Toole et al. |
| 11,311,654 B2 | 4/2022 | O'Toole et al. |
| 11,324,866 B2 | 5/2022 | O'Toole et al. |
| 11,357,893 B2 | 6/2022 | O'Toole et al. |
| 11,357,894 B2 | 6/2022 | O'Toole et al. |
| 11,376,352 B2 | 7/2022 | O'Toole et al. |
| 11,413,380 B2 | 8/2022 | O'Toole et al. |
| 11,717,599 B2 | 8/2023 | Miller et al. |
| 11,806,454 B2 | 11/2023 | De Becdelievre et al. |
| 2001/0044593 A1 | 11/2001 | Lundy |
| 2002/0062103 A1 | 5/2002 | Larsson et al. |
| 2002/0193731 A1 | 12/2002 | Myers et al. |
| 2002/0198489 A1 | 12/2002 | Silver et al. |
| 2003/0069536 A1 | 4/2003 | Greter et al. |
| 2003/0191433 A1 | 10/2003 | Prentiss |
| 2004/0024351 A1 | 2/2004 | Greter et al. |
| 2004/0056641 A1 | 3/2004 | Myers et al. |
| 2004/0074281 A1 | 4/2004 | Lobdell et al. |
| 2004/0087898 A1 | 5/2004 | Weniger |
| 2004/0127845 A1 | 7/2004 | Renz et al. |
| 2004/0267215 A1 | 12/2004 | Charlez et al. |
| 2005/0154349 A1 | 7/2005 | Renz et al. |
| 2005/0219302 A1 | 10/2005 | Vogeley |
| 2005/0228342 A1 | 10/2005 | Yuen |
| 2005/0245860 A1 | 11/2005 | Britto et al. |
| 2006/0106334 A1 | 5/2006 | Jordan et al. |
| 2006/0111664 A1 | 5/2006 | Samson et al. |
| 2006/0122575 A1 | 6/2006 | Wakabayashi |
| 2007/0051172 A1 | 3/2007 | Perinet et al. |
| 2007/0051727 A1 | 3/2007 | Holley |
| 2007/0054651 A1 | 3/2007 | Farmer et al. |
| 2007/0060873 A1 | 3/2007 | Hiraoka et al. |
| 2007/0135761 A1 | 6/2007 | Cheng et al. |
| 2007/0179439 A1 | 8/2007 | Vogelin et al. |
| 2007/0219486 A1 | 9/2007 | Myers et al. |
| 2007/0228059 A1 | 10/2007 | Karsan |
| 2007/0236584 A1 | 10/2007 | Frost-Ruebling et al. |
| 2008/0009815 A1 | 1/2008 | Grabenkort et al. |
| 2008/0090444 A1 | 4/2008 | Luzbetak et al. |
| 2008/0171970 A1 | 7/2008 | Luzbetak et al. |
| 2008/0177224 A1 | 7/2008 | Kelly et al. |
| 2008/0255503 A1 | 10/2008 | Quackenbush et al. |
| 2008/0262420 A1 | 10/2008 | Dao et al. |
| 2008/0275386 A1 | 11/2008 | Myers |
| 2008/0299517 A1 | 12/2008 | Delaney, II |
| 2009/0254028 A1 | 10/2009 | Brittner |
| 2009/0281482 A1 | 11/2009 | Baker et al. |
| 2009/0281485 A1 | 11/2009 | Baker et al. |
| 2010/0292636 A1 | 11/2010 | Renz et al. |
| 2011/0004154 A1 | 1/2011 | Van Schijndel et al. |
| 2011/0009824 A1 | 1/2011 | Yodfat et al. |
| 2011/0071466 A1 | 3/2011 | Silver et al. |
| 2011/0144636 A1 | 6/2011 | Alexander et al. |
| 2011/0196291 A1 | 8/2011 | Vischer et al. |
| 2011/0274566 A1 | 11/2011 | Amirouche et al. |
| 2012/0021068 A1 | 1/2012 | Barness et al. |
| 2012/0035951 A1 | 2/2012 | Goetz et al. |
| 2012/0043065 A1 | 2/2012 | Ranne et al. |
| 2012/0072117 A1 | 3/2012 | Loddoch et al. |
| 2012/0072118 A1 | 3/2012 | Mann |
| 2012/0095599 A1 | 4/2012 | Pak et al. |
| 2012/0109083 A1 | 5/2012 | Coulthard et al. |
| 2012/0116299 A1 | 5/2012 | Tack |
| 2012/0136325 A1 | 5/2012 | Allen et al. |
| 2012/0143879 A1 | 6/2012 | Stoitsev |
| 2012/0165729 A1 | 6/2012 | Cudworth |
| 2012/0220753 A1 | 8/2012 | Gera et al. |

(56) References Cited

U.S. PATENT DOCUMENTS

| | | |
|---|---|---|
| 2012/0277636 A1 | 11/2012 | Blondheim et al. |
| 2012/0277728 A1 | 11/2012 | Weber et al. |
| 2013/0023821 A1 | 1/2013 | Khalil et al. |
| 2013/0123688 A1 | 5/2013 | Bosman et al. |
| 2014/0031744 A1 | 1/2014 | Chen |
| 2014/0052056 A1 | 2/2014 | Garbez et al. |
| 2014/0135683 A1 | 5/2014 | Hradisky et al. |
| 2014/0142501 A1 | 5/2014 | Clark et al. |
| 2014/0227112 A1 | 8/2014 | Felber |
| 2014/0263611 A1 | 9/2014 | Bauer |
| 2014/0275857 A1 | 9/2014 | Toth et al. |
| 2014/0288466 A1 | 9/2014 | Alvarez et al. |
| 2014/0323962 A1 | 10/2014 | Kooijker et al. |
| 2014/0378895 A1 | 12/2014 | Barack |
| 2015/0157775 A1 | 6/2015 | Hu |
| 2015/0212036 A1 | 7/2015 | Jin et al. |
| 2015/0212037 A1 | 7/2015 | Okazaki et al. |
| 2015/0217033 A1 | 8/2015 | Pollen et al. |
| 2015/0217035 A1 | 8/2015 | Pollen et al. |
| 2015/0217036 A1 | 8/2015 | Pollen et al. |
| 2015/0217037 A1 | 8/2015 | Pollen et al. |
| 2015/0283311 A1 | 10/2015 | Alvarez et al. |
| 2015/0314053 A1 | 11/2015 | Furrer et al. |
| 2015/0328380 A1 | 11/2015 | Furrer et al. |
| 2015/0335800 A1 | 11/2015 | Yamashita |
| 2016/0000980 A1 | 1/2016 | Alvarez et al. |
| 2016/0058928 A1 | 3/2016 | Nowroozi et al. |
| 2016/0058929 A1 | 3/2016 | Medvedev et al. |
| 2016/0082165 A1 | 3/2016 | Alvarez et al. |
| 2016/0082166 A1 | 3/2016 | Guthrie et al. |
| 2016/0135998 A1 | 5/2016 | Riesinger |
| 2016/0151551 A1 | 6/2016 | Felber |
| 2016/0158424 A1 | 6/2016 | Chen et al. |
| 2016/0166745 A1 | 6/2016 | Aalders |
| 2016/0174728 A1 | 6/2016 | Karp et al. |
| 2016/0206794 A1 | 7/2016 | Makower et al. |
| 2016/0213824 A1 | 7/2016 | Fridman |
| 2016/0220743 A1 | 8/2016 | Guthrie et al. |
| 2016/0220745 A1 | 8/2016 | Guthrie et al. |
| 2016/0228625 A1 | 8/2016 | Holtz et al. |
| 2016/0256617 A1 | 9/2016 | Hansen |
| 2016/0271305 A1 | 9/2016 | Kurihara et al. |
| 2016/0287767 A1 | 10/2016 | Simmons et al. |
| 2016/0296681 A1 | 10/2016 | Gaskin et al. |
| 2016/0296682 A1 | 10/2016 | Phillips et al. |
| 2016/0304004 A1 | 10/2016 | Sandbothe et al. |
| 2016/0310650 A1 | 10/2016 | Makower et al. |
| 2016/0325031 A1 | 11/2016 | Miller et al. |
| 2017/0021068 A1 | 1/2017 | Gaskin et al. |
| 2017/0035951 A1 | 2/2017 | Tanaka |
| 2017/0043065 A1 | 2/2017 | Takeuchi |
| 2017/0072117 A1 | 3/2017 | Kurihara et al. |
| 2017/0072118 A1 | 3/2017 | Makower et al. |
| 2017/0080135 A1 | 3/2017 | Chen |
| 2017/0095599 A1 | 4/2017 | Kondo et al. |
| 2017/0112983 A1 | 4/2017 | Thorne et al. |
| 2017/0136161 A1 | 5/2017 | Alvarez et al. |
| 2017/0143879 A1 | 5/2017 | Okaguchi |
| 2017/0173232 A1 | 6/2017 | Chang et al. |
| 2017/0173233 A1 | 6/2017 | Tanaka |
| 2017/0216505 A1 | 8/2017 | Kim |
| 2017/0220753 A1 | 8/2017 | Guthrie et al. |
| 2017/0292509 A1 | 10/2017 | Kurihara et al. |
| 2018/0008758 A1 | 1/2018 | Garbez et al. |
| 2018/0021490 A1 | 1/2018 | Chang et al. |
| 2018/0021491 A1 | 1/2018 | Rigert et al. |
| 2018/0028733 A1 | 2/2018 | Rigert et al. |
| 2018/0104396 A1 | 4/2018 | Park |
| 2018/0110900 A1 | 4/2018 | Korenfeld |
| 2018/0110906 A1 | 4/2018 | Barack |
| 2018/0154055 A1 | 6/2018 | Alvarez et al. |
| 2018/0333523 A1 | 11/2018 | Chang et al. |
| 2018/0361040 A1 | 12/2018 | O'Toole et al. |
| 2019/0209748 A1 | 7/2019 | Analytis et al. |
| 2019/0275222 A1 | 9/2019 | Evans et al. |
| 2019/0365966 A1 | 12/2019 | Bächler et al. |
| 2020/0016307 A1 | 1/2020 | Edelman et al. |
| 2020/0300237 A1 | 9/2020 | Marbet et al. |
| 2021/0030934 A1 | 2/2021 | Zhang |
| 2021/0077673 A1 | 3/2021 | Mason et al. |
| 2021/0093761 A1 | 4/2021 | Hwang et al. |
| 2021/0170080 A1 | 6/2021 | O'Toole et al. |
| 2021/0196873 A1 | 7/2021 | O'Toole et al. |
| 2021/0196874 A1 | 7/2021 | O'Toole et al. |
| 2021/0196875 A1 | 7/2021 | O'Toole et al. |
| 2021/0196876 A1 | 7/2021 | O'Toole et al. |
| 2021/0205511 A1 | 7/2021 | O'Toole et al. |
| 2021/0205512 A1 | 7/2021 | O'Toole et al. |
| 2021/0205513 A1 | 7/2021 | O'Toole et al. |
| 2021/0205514 A1 | 7/2021 | O'Toole et al. |
| 2021/0205515 A1 | 7/2021 | O'Toole et al. |
| 2021/0205516 A1 | 7/2021 | O'Toole et al. |
| 2021/0205517 A1 | 7/2021 | O'Toole et al. |
| 2021/0205518 A1 | 7/2021 | O'Toole et al. |
| 2021/0228789 A1 | 7/2021 | O'Toole et al. |
| 2021/0268158 A1 | 9/2021 | O'Toole et al. |
| 2022/0031918 A1 | 2/2022 | Quackenbush |
| 2022/0409782 A1 | 12/2022 | Höner et al. |
| 2023/0111110 A1 | 4/2023 | De Becdelievre et al. |
| 2023/0143842 A1 | 5/2023 | O'Toole et al. |
| 2023/0158215 A1 | 5/2023 | De Becdelievre et al. |
| 2023/0338630 A1 | 10/2023 | Claassen et al. |

FOREIGN PATENT DOCUMENTS

| | | |
|---|---|---|
| CN | 101549180 A | 10/2009 |
| CN | 105233355 A | 1/2016 |
| CN | 105288759 A | 2/2016 |
| CN | 205626591 U | 10/2016 |
| CN | 205913571 U | 2/2017 |
| CN | 206473606 U | 9/2017 |
| CN | 109621041 A | 4/2019 |
| CN | 209033304 U | 6/2019 |
| CN | 210096493 U | 2/2020 |
| DE | 3311982 C2 | 12/1986 |
| DE | 19750620 A1 | 6/1999 |
| EP | 0503280 A2 | 9/1992 |
| EP | 1586340 A2 | 10/2005 |
| EP | 1430918 B1 | 5/2008 |
| EP | 2436277 A1 | 4/2012 |
| EP | 2502640 A1 | 9/2012 |
| EP | 2210628 B1 | 2/2013 |
| EP | 1404393 B1 | 12/2014 |
| EP | 2077868 B1 | 7/2016 |
| EP | 1263487 B2 | 11/2016 |
| EP | 3299043 A1 | 3/2018 |
| EP | 3482782 A1 | 5/2019 |
| EP | 4000661 A1 | 5/2022 |
| GB | 2435617 B | 3/2008 |
| GB | 2473022 B | 12/2011 |
| GB | 2499248 B | 4/2014 |
| JP | H11178917 A | 7/1999 |
| JP | 2000350527 A | 12/2000 |
| JP | 2007501673 A | 2/2007 |
| JP | 2013545519 A | 12/2013 |
| JP | 2014529312 A | 11/2014 |
| JP | 2014532498 A | 12/2014 |
| JP | 2016010524 A | 1/2016 |
| JP | 2016508804 A | 3/2016 |
| JP | 2016514516 A | 5/2016 |
| JP | 2016524490 A | 8/2016 |
| JP | 2016526396 A | 9/2016 |
| JP | 2017503552 A | 2/2017 |
| JP | 2017509379 A | 4/2017 |
| JP | 6292720 B2 | 3/2018 |
| RU | 2344380 C1 | 1/2009 |
| RU | 2441367 C2 | 2/2012 |
| WO | WO 1990000413 A1 | 1/1990 |
| WO | WO-9420158 A1 | 9/1994 |
| WO | WO-9625187 A1 | 8/1996 |
| WO | WO-9636298 A1 | 11/1996 |
| WO | WO 2002102437 A2 | 12/2002 |
| WO | WO-2004108184 A2 | 12/2004 |
| WO | WO-2005079441 A2 | 9/2005 |

(56) References Cited

FOREIGN PATENT DOCUMENTS

| | | |
|---|---|---|
| WO | WO-2005114113 A2 | 12/2005 |
| WO | WO-2005114116 A1 | 12/2005 |
| WO | WO-2005114113 A3 | 3/2006 |
| WO | WO 2008137678 A1 | 11/2008 |
| WO | WO-2009134271 A1 | 11/2009 |
| WO | WO-2013064852 A1 | 5/2013 |
| WO | WO-2014094187 A1 | 6/2014 |
| WO | WO-2014160614 A1 | 10/2014 |
| WO | WO-2015069095 A1 | 5/2015 |
| WO | WO-2015081459 A1 | 6/2015 |
| WO | WO-2015116749 A1 | 8/2015 |
| WO | WO-2015120321 A1 | 8/2015 |
| WO | WO-2015150225 A1 | 10/2015 |
| WO | WO-2015174330 A1 | 11/2015 |
| WO | WO-2016002606 A1 | 1/2016 |
| WO | WO-2016006458 A1 | 1/2016 |
| WO | WO-2016006494 A1 | 1/2016 |
| WO | WO-2016006496 A1 | 1/2016 |
| WO | WO-2016007560 A1 | 1/2016 |
| WO | WO-2016007561 A1 | 1/2016 |
| WO | WO-2016010524 A1 | 1/2016 |
| WO | WO-2016014469 A1 | 1/2016 |
| WO | WO-2016014488 A1 | 1/2016 |
| WO | WO 2016014494 A1 | 1/2016 |
| WO | WO-2016024558 A1 | 2/2016 |
| WO | WO-2016025405 A1 | 2/2016 |
| WO | WO-2016039083 A1 | 3/2016 |
| WO | WO-2016104673 A1 | 6/2016 |
| WO | WO-2016108616 A1 | 7/2016 |
| WO | WO-2016164853 A1 | 10/2016 |
| WO | WO-2016186452 A1 | 11/2016 |
| WO | WO-2017061349 A1 | 4/2017 |
| WO | WO-2017108555 A1 | 6/2017 |
| WO | WO 2017139437 A1 | 8/2017 |
| WO | WO-2017139480 A1 | 8/2017 |
| WO | WO-2017190678 A1 | 11/2017 |
| WO | WO 2018054758 A1 | 3/2018 |
| WO | WO-2018229504 A1 | 12/2018 |
| WO | WO 2019080995 A1 | 5/2019 |

OTHER PUBLICATIONS

Amended Complaint in *Shenzhen Root Technology Co., Ltd.* v. *Chiaro Technology, Ltd.*, WDWA-2-23-cv-00631, filed Jun. 2, 2023; 24 pages.
Extended European Search Report issued in European Application No. 22174446.9, mailed Oct. 11, 2022, 26 pages.
GB Search Report, dated Nov. 15, 2017, issued in priority GB Application No. GB1709561.3, 4 pages.
GB Search Report, dated Nov. 28, 2017, issued in priority GB Application No. GB1709566.2, 3 pages.
GB Search Report for , dated Nov. 29, 2017, issued in priority GB Application No. GB1709564.7, 4 pages.
International Search Report issued in International Application No. PCT/GB2021/050764, mailed Jul. 6, 2021, 5 pages.
International Search Report issued in PCT/GB2018/051659 dated Dec. 4, 2018, 9 pages.
Japanese Search Report issued in Japanese Application No. 2020519188, mailed Jun. 24, 2022, 20 pages.
The Best Hands-Free Breast Pumps, posted at healthline.com, earliest date posted on Aug. 24, 2020, [online], acquired on Oct. 30, 2021, Available on internet. url: https://www.healthline.com/health/parenting/breast-feeding/best-hands-free-breast-pumps#Best-hands-free-breast-pumps (Year: 2020), 11 pages.
Whisper Wear Hands-Free Breast Pump, Model: WWWPMP01, UserGuide,pp. 1-20 , Distributed with product atleast as early as 2007 (see https://web.archive.org/web/20070621162539/http://www.whisperwear.com/pump_single.html ), 10 pages.
Declaration of Ryan Bauer in Support of Petition for Inter Partes Review of U.S. Pat. No. 11,413,380, Exhibit 1005 in IPR2024-00953, May 31, 2024; 137 pages.
Amended Claims in Response to Rule 71(3) (clean) regarding European Patent Application No. 18741597.1 to Positec Power Tools (Suzhou) Co. Ltd; dated Feb. 20, 2024; 4 pages.
Breastfeeding and the Use of Human Milk, American Academy of Pediatrics, Pediatrics, vol. 100, No. 6, Dec. 6, 1997; pp. 1035-1039.
Courage, Katherine, "The Sucky History of the Breast Pump," Innovation, Smithsonian Magazine, Sep. 12, 2022; 17 pages. Available at: https://www.smithsonianmag.com/innovation/sucky-history-of-the-breast-pump-180980653/.
GB 201709566.2 entitled 'Breast Pump' filed Jun. 15, 2017; 44 pages (Priority Document 1).
GB201709564.7 entitled 'A Liquid Level Measurement System' filed Jun. 15, 2017; 24 pages (Priority Document 2).
GB 201709561.3 entitled 'Bra Clip' filed Jun. 15, 2017; 24 pages (Priority Document 3).
GB 201809036.5 entitled 'Breast Pump System' filed Jun. 1, 2018; 169 pages (Priority Document 4).
Illinois Nursing Mothers in the Workplace Act, Illinois General Assembly, Jul. 12, 2001; 2 pages. Available at: https://www.ilga.gov/legislation/ilcs/ilcs3.asp?ActID=2429.
Omnexus, "Silicone Rubber: Complete Guide on Highly Durable Elastomer" Feb. 28, 2024, [cited Feb. 28, 2024] Available from: [https://omnexus.specialchem.com/selection-guide/silicone-rubber-elasto].
Reply to communication under Rule 71(3) regarding European Patent Application No. 18741597.1 to Positec Power Tools (Suzhou) Co. Ltd, dated Feb. 20, 2024; 1 page.
Sex Descrimination—Breastfeeding and Expressing Milk, British Columbia Human Righs Commission Policy and Procedure Manual, Aug. 1, 2000; 2 pages. Available at: http://www.infactcanada.ca/br_bc_humanrights.htm.
Women's Health Today, "How to Choose a Breast Pump" Nov. 8, 2017, 8 pages; Available from: [https://womenshealthtoday.blog/2017 /11 /08/how-to-choose-a-breast-pump/] original file name: D2 How to Choose a Breast Pump_Womens Health Today.pdf.
Wyatt, Stephanie, MSN, APN, "Challenges of the Working Breastfeeding Mother, Workplace Solutions," AAOHN Journal, vol. 50, No. 2, Feb. 2022; pp. 61-66.
Exhibit List for IPR 2024-01296 (Declaration of Ryan Bauer U.S. Pat. No. 11,413,380) Feb. 14, 2024, 142 pages.
International Search Report and Written Opinion for Application No. PCT/EP2023/073973, mailed on Dec. 4, 2023, 9 pages.
International Search Report and Written Opinion for Application No. PCT/EP2023/073975, mailed on Dec. 19, 2023, 9 pages.
Declaration of Ryan Bauer in Support of Request for Reexamination of U.S. Pat. No. 11,357,893 Under 35 U.S.C. § 302 and 37 C.F.R. § 1.510, in the United States Patent and Trademark Office, Sep. 24, 2024; 233 pages.
CNET, "Pump on the go with the willow breast pump" 4 pages.
D'Ignazio, C., et al., A Feminist HCI Approach to Designing Postpartum Technologies: "When I first saw a breast pump I was wondering if it was a joke," Proceedings of the 2016 CHI Conference on Human Factors in Computing Systems, Association for Computing Machinery, San Jose, California, USA, 11 pages (May 2016).
Falcone, J., "CES 2017: The final word" CNET, 18 pages (2017).
Ingraham, N., "How a smart breast pump won CES," Engadget, 11 pages.
Larson, S., "Smart breast pump lets moms multitask," CES 2017: Willow's smart breast pump lets moms multitask, 16 pages.
Laughlin, S., "Willow is among several companies at CES focused on meeting the needs of new moms," CES 2017: Maternal tech, 6 pages (Jan. 2017).
Martin, C. E., and Cary, J., "Shouldn't the Breast Pump Be as Elegant as an iPhone and as Quiet as a Prius by Now?" Motherlode: Adventures in Parenting, 3 pages (Mar. 2014).
"Medela Pump In Style Advanced—Review" The Pumping mommy, 8 pages.
Strauss, E., "Breast Pumps Are Finally Getting Better. Here's How," Slate, 7 pages (May 2016).
"The Breast Pump Finally Joins the 21st Century," Arielle Pardes, 18 pages (2017).

(56) References Cited

OTHER PUBLICATIONS

The Willow smart breast pump could be a game-changer for moms, 2 pages.
Willow breast pump at CES 2017, 2 pages.

* cited by examiner

|  | Example 1 | Example 2 |
|---|---|---|
| Calibration phase | | |
| 302 Run pump to threshold | Threshold pressure | Threshold number of rotations |
| 304 Measure | Number of rotations to reach threshold pressure | Pressure in container after threshold rotations |
| Derive | Derive volume of air pumped out using change in pressure, volume of container and ideal gas law | Derive moles pumped out using ideal gas law |
| 308 Derive operation equation | Derive operation equation relating volume pumped to revolutions to hit threshold pressure | Derive operation equation relating moles pumped out to pressure change per threshold revolutions |
| Measurement phase | | |
| 404 Run pump to threshold | Threshold pressure in container | Threshold number of rotations |
| 406 Measure | Number of rotations to reach threshold pressure | Pressure after threshold rotations |
| 408 Calculate using measurement and operation equation | Volume of air pumped out | Moles pumped out |
| 410 Use ideal gas law to Calculate | Volume of air left in container | Volume of air left in container |
| 412 Calculate volume of milk | $Volume_{container} - Volume_{air}$ | |

FIG. 5

MEASUREMENT SYSTEM

CROSS-REFERENCE TO RELATED APPLICATIONS

The present application is a continuation of U.S. application Ser. No. 18/445,457. Filed Aug. 31, 2023, which claims priority to GB Application No. 2212673.4, filed Aug. 31, 2022, which are incorporated herein in their entirety by reference.

FIELD

The present disclosure relates to a measurement system for measuring fluid in a container and, in particular, to a milk measurement system.

BACKGROUND

A breast pump system is a mechanical or electro-mechanical device that extracts milk from the breasts of a lactating person.

Breast pumps for expressing human breast milk are known. Vacuum is used to simulate suction generated by a feeding child. Milk is expressed from the breast and into a milk collection container. It is useful to measure the quantity of expressed milk. One way to do this is to have a clear container for the breast pump, through which the level of expressed milk inside the container can be seen. However, viewing the milk bottle is not always possible, for example in a breast pump that collects milk while being worn inside a maternity bra. Additionally, it may not always be accurate, since it depends on, for example, the angle of the container.

SUMMARY

Aspects and features of the present disclosure are set out in the accompanying claims.

BRIEF DESCRIPTION OF THE DRAWINGS

Specific embodiments are described below by way of example only and with reference to the accompanying drawings in which:

FIG. 5 shows example measurement methods;

DETAILED DESCRIPTION OF THE EMBODIMENTS

Overview

The present disclosure relates to a method and system of determining the amount of liquid in a container. In some embodiments, the disclosure relates to methods and systems of determining the amount of milk in a container of a breast pump.

The pressure of a gas in a sealed container is a function of the quantity of gas (mass or no. of molecules/moles), the composition of the gas, the volume it occupies and the temperature. The inventors of the present disclosure have created a system in which, by manipulating these variables (quantity of gas, composition of the gas, volume it occupies or temperature) by a known amount and then measuring the pressure, the air volume in the container is determined. If the liquid container volume is a known volume size, the liquid volume can then be calculated by subtracting the air volume from the known container volume.

Some examples of possible methods of implementing this idea are as follows. The following are merely illustrative examples and not an exhaustive list of options:

Add or remove a known quantity of gas to a container using an air pump and monitor the associated change in pressure.

Change the volume of the container by a known amount and monitor the associated change in pressure.

Connect the container to another container of known volume at a different pressure to the first container (changing both the container volume and quantity of gas by known amounts).

Pump the container up to a known pressure and subsequently release back towards atmospheric pressure through a known orifice diameter. By measuring the rate of pressure decay, the quantity of gas in the bottle volume can be determined.

A number of these examples will be described below.

A system and method for measuring the amount of fluid in a container is described herein. Specific examples of a milk measurement device for measuring the amount of milk in a container of a breast pump are described. The disclosed systems and methods may be used to measure the amount of fluid in a container in other applications, and the disclosure is not limited to measuring the amount of milk from a breast pump. For example, the disclosed embodiments may be used to measure the amount of fluid in a negative pressure wound apparatus.

Figure 1:
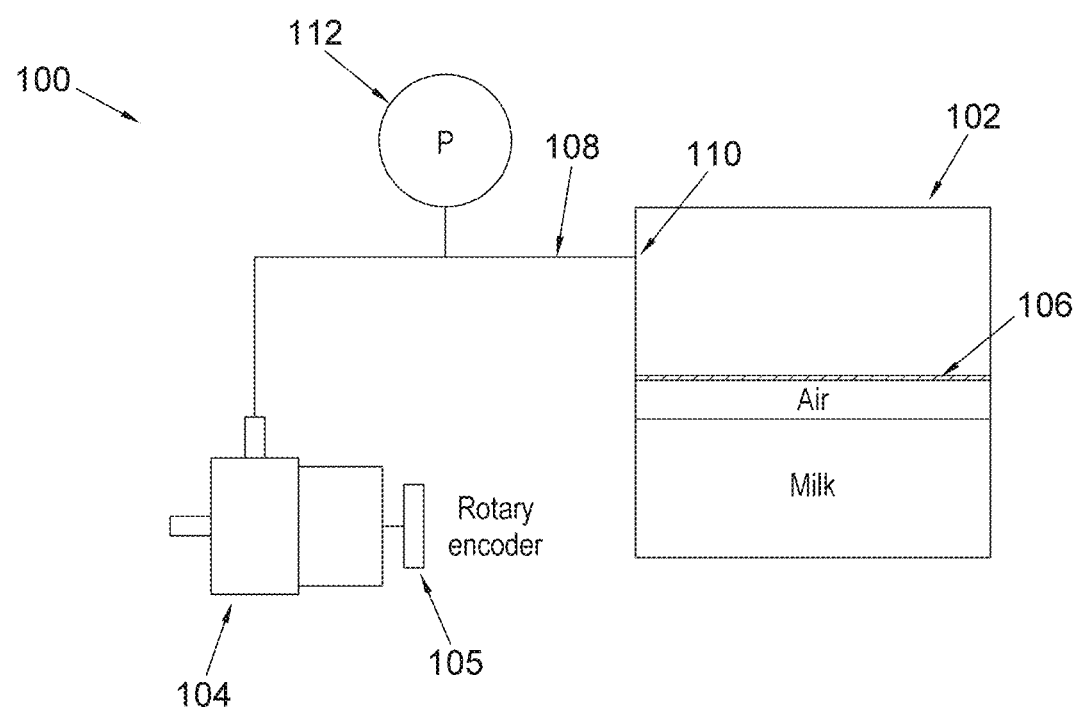
FIG. 1 shows a milk measurement system according to an embodiment of the invention.

A milk measurement system according to some embodiments is shown in FIG. 1. The milk measurement system is for detecting the volume of liquid inside a container of a breast pump.

The milk measurement system 100 may be part of a breast pump suitable for expressing human breast milk. The assembled breast pump system may be shaped to substantially fit inside a bra. The breast pump may be configured as a self-contained, in-bra wearable device.

FIG. 1 illustrates a milk measurement system according to some embodiments. A milk container 102 may be connected to a pump 104. The milk container has a known volume. The milk container may be any shape and size, although in some embodiments is shaped to fit inside the bra of the user. The terms milk container and milk bottle (or simply "bottle") may be used interchangeably herein.

In this description the term vacuum is used to refer to a negative air pressure. A negative air pressure is defined as any pressure below that of the surrounding air environment. In other words, a negative air pressure is a pressure lower than the system of the breast pump when the air pump has not been used to remove air from the system. A typical air pressure, or atmospheric pressure, of a standard environment is 760 mmHg (varies subject to atmospheric conditions, such as weather, altitude, temperature), therefore a vacuum may be defined as any pressure lower than the local current atmospheric pressure.

A "stronger vacuum" is used to refer to a larger negative pressure, and a "weaker vacuum" is used to refer to a smaller negative pressure. If a vacuum reduces, then the vacuum changes from a stronger vacuum (larger negative pressure) to a weaker vacuum (smaller negative pressure). When a vacuum reduces, the actual pressure in the container increases (the pressure is a smaller negative value). A vacuum reduces when fluid, such as milk or air, is let into a container. Similarly, a vacuum increases when fluid (such as air) is removed from the container.

In some embodiments, the pump 104 is configured to pump air into or from the container 102.

A pump is typically an electromechanical device that moves a fluid. In the present disclosure, the pump is a positive displacement air pump, however the disclosure is not limited to this style of pump. A positive displacement pump moves a fluid by repeatedly enclosing a fixed volume and moving it mechanically through the system. The pumping action is cyclic and can be driven by pistons, screws, gears, rollers, diaphragms or vanes. The pump can be driven by a motor, piezoelectric crystal, magnetic solenoid for example.

In some implementations, the pump is a vacuum pump, or negative pressure pump, configured to pump air from the container 102. In these embodiments, the pump 104 reduces the pressure in the container (creating a negative pressure in the container). In some other implementations, the pump is a positive pressure pump, configured to pump air into the container 102. In such embodiments, the pump increases the pressure in the container.

The air pump is a mechanical air pump designed to either extract air from a breast pump system or insert air into a breast pump system. In the present disclosure, the air pump is configured to draw air out of the breast pump system and create a negative air pressure in the nipple tunnel. When the air pump is activated, negative air pressure is created between the air pump, the milk container and the breast shield, thereby applying negative pressure to the nipple, drawing milk from the breast, and collecting it inside the milk container.

The air pump can be any type of pump that moves air. A method for quantifying how much air has been pumped is also required. The volume of gas moved by the pump can be measured directly with a separate flow meter or by characterising the pump so as to estimate the volume of gas pumped as a factor of the number of pump cycles counted, or alternatively by measuring the time the pump is running for. Therefore the air pump comprises a pump which pumps air. The pump may comprise a sensor which measures the number of oscillations of the pump, a timer which measures the time of operation, or an external flow sensor.

Counting the number of pump cycles can be achieved in a number of ways, including:
- Rotary encoder on the end of the pump's electric motor
- Linear encoder directly counting piston oscillations
- Estimating motor rotations by characterising rotations as a factor of motor drive (voltage, current etc) parameters.
- As the cyclical nature of the pump changes the pressure in the container in "pulses", if you were to measure the pressure in the container at a high enough sample rate and resolution, you could sense the pulsation frequency, which directly corresponds to the pump cycle rate.
- Specifically referring to pumps driven electronically by pulses (piezoelectric, solenoid etc); by measuring the cycle rate of the electronic drive circuit used to control the pump.
- Use the Back Electromotive Force to estimate a brushed or brushless motor speed, and therefore give the ability to count the number of rotations in a given time frame.

A formula which characterises the volume of air moved by the pump as a factor of the pump cycles measured can be determined in many ways. It could be derived theoretically based on the pump's piston volume, container pressure and valve behaviour. Alternatively this equation can be derived experimentally, which has the potential benefit of compensating for pump manufacturing variation when mass produced. Deriving an equation is discussed below in the "calibration" phase of FIGS. 2 and 3.

In FIG. 1 the air pump is a rotary diaphragm pump according to some embodiments. A rotary diaphragm pump is a positive displacement pump that uses a combination of the reciprocating action of a deformable diaphragm and suitable valves on either side of the diaphragm to pump a fluid. In the case of the present disclosure the rotary diaphragm pump pumps air. A rotary air pump provides a cost effective and easy way to reach desired pressures. In this case, the air pumping subsystem may either be configured as an open loop or closed loop pumping subsystem. Closed loop pumping means that there is a way to run the pump until a threshold value has been sensed. This threshold could be pressure reached, pump oscillations reached, threshold time of operation, or total air flow pumped as examples, but not an exhaustive list of options. Open loop pumping means the pump is run until switched off—typically using time to determine when to turn the pump off. The rotary diaphragm pump used may be a standard rotary diaphragm pump. The deformable diaphragm may be made of silicone, rubber or thermo-elastomer for example.

In some embodiments, there is a controller (shown in FIG. 7) configured to control operation of the pump. The controller 700 may comprise computer readable instructions configured to control operation of the pump. The controller may also comprise a memory. The memory is configured to store configuration and factory settings as well as session data. The data may be communicated to external devices through a wireless or wired connection.

The rotary diaphragm pump may comprise a rotary encoder 105. The rotary encoder converts information about the number of pump motor rotations, and therefore its speed, and number of rotations to an output signal. The pump motor rotation count relates to the pump cycles completed. In some embodiments, the pump does not comprise a rotary encoder and other means of determining the volume of air pumped, such as an external flow rate sensor, is included.

The pump can be controlled to run to a threshold number of pump rotations. The pump is run and the rotary encoder is used to count the number of pump rotations. Once the threshold number of rotations is reached, the pump is stopped.

In some embodiments, a brushless motor could be used. A brushless motor's rotational speed is directly controlled by the electronic drive circuitry (whereas a brushed motor needs an external encoder to sense the speed it reaches). In this embodiment, the motor speed and rotational count can be measured directly from the drive circuitry.

In some embodiments, a piezo pump is used, wherein the pump comprises a means for counting the number of times the electronic drive circuit oscillates the piezo.

Any conceivable pump may be used. The number of oscillations, rotations or cycles of the pump are measured. The terms "oscillations" and "cycles" are used throughout to cover any cycle of a pump which works using repeat cycles or oscillations. These terms may be used interchangeably and refer to both linear and rotational oscillations or cycles.

The pump is configured to operate quietly in normal use. A cavity containing the pump may be sealed so as to further attenuate sound.

The measurement system 100 may be part of a breast pump which additionally comprises a breast shield (not shown) configured to fit to a user's breast. A seal is created between the user's breast and the breast shield. The breast shield may include a nipple tunnel for receiving a user's nipple. A negative pressure, or a "pumping vacuum," is created in the nipple tunnel to simulate suction of a feeding child and express milk from the nipple.

The breast shield and the milk container may be directly removable from or attachable to a housing in normal use or during normal dis-assembly. The breast shield (not shown) may comprise a breast flange for fitting to the user's breast and a nipple tunnel for receiving a nipple. The breast flange contacts the user's breast and seals the breast shield to the surface of the user's breast. The breast flange may be a funnel or conical shape. The nipple tunnel may be a tubular shape extending from the breast flange. The nipple tunnel may also feasibly be other shapes such as a cuboid, triangular or cylinder.

The volume of air (or gas) in the system determines the time taken to reach a threshold pressure at a given pump speed. Therefore reducing the air volume in the system ensures that the maximum vacuum pressure generated in the system, such as in the nipple tunnel, can be achieved more quickly. It is also desirable to reduce excess air volume in the system to enable performance gains such as reducing noise levels during the operation of the air pump and increasing efficiency of milk production. In some embodiments, the breast shield is designed to be flexible so that it may collapse and expand when exposed to different pressures generated by the air pump.

In some embodiments, milk is expressed into the nipple tunnel and travels along a milk path from the nipple tunnel to the container 102. Pressure differentials and a non-return valve may be used to cause the milk to flow along the milk path from the nipple tunnel to the container 102.

In some embodiments, the pump 104 is used to create the pumping vacuum in the nipple tunnel. The pump can be connected to the nipple tunnel and run at a first level of intensity to create the necessary pumping vacuum. In some embodiments, a separate pump is used to create the pumping vacuum, and the system comprises two pumps, one pump 104 comprising in the measurement system 100, and a second pump to create a pumping vacuum in the nipple tunnel. The maximum pumping vacuum may be in the region from −200 mmHg to −300 mmHg.

There may also be a "base level vacuum" created in the breast shield, specifically in the nipple tunnel. The base level vacuum is a minimum pressure level which is maintained throughout use of the pump to maintain the seal between the user's breast and the breast shield, and to maintain a tight fit on the user's breast. The base level vacuum may be in the region of −25 mmHg to −75 mmHg.

The base level vacuum may be created by the pump of the milk measurement system 104. In other embodiments, the base level vacuum is created by a separate pump, which may or may not be the same pump which creates the pumping vacuum in the nipple tunnel.

In embodiments where the same single pump is used in the measurement system, to create the pumping vacuum pressure and to create the base level vacuum pressure, the pump is configured to pump until different levels of pressures have been achieved. A first level of pumping pressure is provided to generate the base level vacuum inside the nipple tunnel. A second level of pumping pressure is provided to generate a pumping vacuum to initiate milk expression from the breast. The second level of pumping pressure is more intense than the first level. This is because a greater negative air pressure must be generated for when the air pump is expressing milk from the user's breast, compared to when only the base level vacuum desired pressure is required. A third level of pumping pressure is provided to pump air at an intensity for the purpose of measuring the amount of milk in the container, as will be explained in this disclosure. The third level of pumping pressure may be equal or different to the first level of pumping pressure.

The milk container 102 may be designed to receive the breast milk from the nipple tunnel and store the breast milk whilst the user continues to operate the breast pump. The milk container is a reusable container that is connected to the housing. It is possible that the milk is added straight into this container, or into a disposable milk bag which sits inside the rigid container. In some embodiments, the milk container has an external surface shaped to continue a curved or breast-like shape of the pump. The milk container may be rigid and have a fixed volume.

There may be a flexible diaphragm 106 within the milk container 102 or outside of the milk container. The flexible diaphragm may instead be an air permeable waterproof membrane, and may be hydrophobic and/or oleophobic, for example PTFE. The flexible diaphragm separates the 'wet side' of the system, which the milk contacts, from the 'dry side' which does not come into contact with the milk. The flexible diaphragm may consist of a flexible membrane separating the dry from the wet side, or the flexible membrane may be a disposable milk bag.

In some embodiments, milk enters the container 102 at an entry point (not shown). The pump 104 may be connected to the container 102 via a vacuum port 110, which may be connected to a flow path 108, which may be a tube. The port 110 may be located in the container on the "dry side" of the diaphragm. That is, the vacuum port is located in the container on one side of the diaphragm, and the milk entry point is located in the container on the other side of the diaphragm 106. In this way, milk is prevented from reaching the pump 104.

The diaphragm 106 may also be used in configurations as part of a system to create negative pressure in the nipple tunnel.

In some embodiments, a pressure sensor 112 is connected to the container 102. The pressure sensor is configured to sense and output the pressure in the container 102. In the embodiment in FIG. 1, the pressure sensor is positioned on the flow path between the pump 104 and the container 102. The pressure sensor 112 may alternatively be positioned elsewhere in the system, attached to the container to measure the pressure in the container. In some embodiments, the pressure of the fluid liquid inside the container could be used instead, for example measuring the wet side air pressure.

The pressure sensor 112 may be used to assist in the measurement of milk collection in the milk container 104, by calculating pressure changes in the milk container 104. The pressure sensor is configured to output measurement of the pressure to a processor, for example a processor in a controller.

In some embodiments which will be described in more detail, measurement values from the pressure sensor 112 may be used by the controller to control the pump 104. For example, the controller may control the pump to pump air to/from the container 102 until the container reaches a threshold pressure. In this method, the pump 104 is activated and pumps air until the pressure sensor 112 outputs a measurement of pressure in the container of the threshold pressure. When the controller receives a signal from the pressure sensor 112 that the threshold pressure has been reached, it controls the pump 104 to stop pumping air to/from the container. Alternatively, when the pump is running the rate of change of pressure is measured (by measuring the pressure at a number of different points in time to determine the change in pressure over time). The rate of change or pressure is used to determine the time at which a threshold pressure will be met. The pump is turned off at the predicted time at which the threshold pressure will be met.

During use of the breast pump to pump milk, milk enters the milk container via a milk flow path from the nipple tunnel (not shown). A non-return value ensures that fluid (air, or liquid) cannot leave the container along the milk flow path. The non-return valve allows air and milk to be pulled from the nipple tunnel into the milk container. Once this air and/or milk has passed through the non-return valve it is not possible for it to flow back in the opposite direction (i.e. back towards the nipple tunnel). Therefore, this fluid is permanently extracted from the nipple tunnel. Once fluid has entered the container 102 via the milk path, the only path for air to leave the container is the connection to the pump 104 or when the sealed container is emptied (opening not shown). Fluid flowing into the container via the milk path will increase the pressure in the container. The only way to decrease the pressure in the container during use is through pumping fluid out of the container 102 using pump 104.

The controller (not shown) may be physically contained in the milk measurement system, or may be at a remote location and configured to operate the milk measurement system wirelessly. If the controller is at a remote location, the milk measurement system will have a transmitter/receiver to control the pump and to receive measurement values from the pump sensor (e.g. rotary encoder 105) and the pressure sensor 112.

When a user is pumping milk, it is useful to know the volume of milk which has been pumped. This will allow the user to know how full the container is, and whether or not the container needs emptying. It also can be used in other measurements, such as determining flow rate of milk being pumped. These measurements will enable users of the pump to track their milk supply and the volume of milk being fed to the infant.

Figure 2:
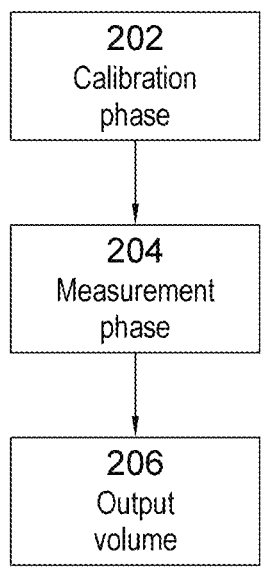
FIG. 2 shows a measurement method according to an embodiment of the invention.

FIG. 2 shows a method of determining the volume of fluid in the container of the milk measurements system of FIG. 1.

Note that throughout this disclosure the fluid referred to is milk, and the measurement system is shown as part of a breast pump for pumping breast milk. However, the measurement system and principles disclosed herein may be used to measure the volume of any liquid in a sealed container.

The method 200 is a method of measuring the volume of liquid in a container. The method may be performed using the milk measurement system of FIG. 1. The method may be partially or wholly implemented by a controller. The method may be a computer-implemented method, performed by a processor in a controller of the system. The processor may comprise computer-executable instructions which, when executed by the processor, cause the processor to perform the steps of the method. This disclosure also relates to transitory and/or non-transitory computer-readable medium which, when executed by a processor, cause the processor to perform steps of the method. This is true for all computer-executed methods disclosed in this application.

In some embodiments, the method begins with a calibration phase 202. The calibration phase happens before a milk pumping session begins (although not necessarily immediately before a session begins). The calibration phase is used to determine an operation formula which is relied upon later in the measurement phase. Whether or not a calibration phase is necessary depends on the techniques employed in the measurement phase (the measurement phase is described below). In embodiments where the measurement phase employs a technique running the pump and measuring parameters of the pump, then a calibration phase may be needed to determine an operation equation for the pump. Depending on the technique employed in the measurement phase, a calibration phase may be used to determine an operation equation of other components instead.

In some embodiments, the calibration phase is not required. An operation equation may be determined in other ways. For example, an operation value for a pump may be determined for the type of pump at the manufacturing phase, and stored in the pump controller. Alternatively, in other techniques a calibration phase is not needed to determine an operation equation. Scenarios are described below in detail, but, for example, in place of using a calibration phase to determine the amount of air pumped by the pump, the amount of air can be determined through different calculations, for example by monitoring the size of the piston in its fully extended and contracted position and the pressure in the attached cavity to calculate the volume of air pumped.

In some embodiments, a calibration phase is used to determine an operation equation for use in calculating the volume of air in the container during use of the pump. The calibration phase may be performed with an empty container or empty containers, as will be explained later. The calibration stage is performed before a milk pumping session has begun. The calibration phase may take place before a breast pump system has been provided to the user, for example in a factory setting. The calibration phase may be a one-off phase run once when the pump is manufactured. In this scenario, the operation formula determined using the calibration phase is used throughout the lifetime of the pump, and each pumping session relies on the operation formula determined from the original calibration phase. Alternatively the calibration phase may be performed multiple times throughout the lifetime of the pump. In this scenario a user may perform the calibration phase prior to pumping.

In some embodiments, discussed more below, the calibration phase may be performed once at the beginning of the lifetime of the pump to determine an operation formula. During the lifetime of the pump, between pumping sessions, a recalibration phase is performed, where the operation formula is updated. This is used to ensure the operation formula remains accurate throughout the lifetime of the pump. It is not necessary for a calibration phase to be performed before each pumping session.

Figure 3:
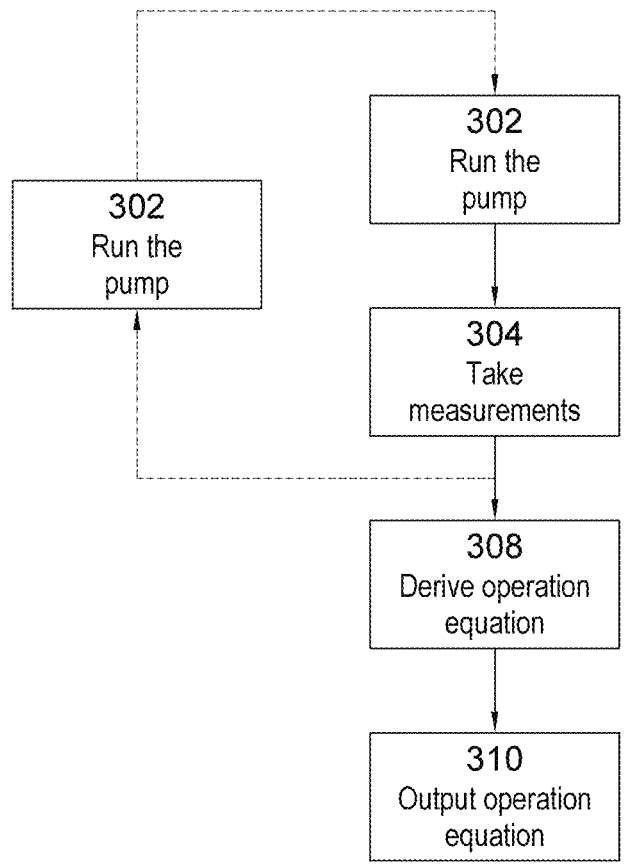
FIG. 3 shows a calibration phase according to an embodiment of the invention.

The calibration phase is discussed in more detail in FIG. 3. The calibration phase may be performed with a container of known air volume, or multiple containers each of known air volumes. In some implementations a single container of known air volume may be used, with known amounts of liquid incrementally added. In effect, adding a known volume of liquid to a container with a known volume to change the air volume would create the same effect as multiple containers of known air volumes. The calibration phase is used to determine an operation equation for the pump by pumping air to/from the container, and measuring the number of pump rotations and the change in pressure. Instead of measuring the number of pump rotations, the time that the pump is running for may be measured instead. Running the calibration phase on multiple air volumes (either through using multiple containers of different size, or through adding liquid to the container to change the internal air volume) increases the accuracy of the operation equation which is determined.

In some embodiments, after the calibration phase, 202, is a measurement phase 204. Details of the measurement phase are given in FIG. 4. In the measurement phase, milk is pumped into a container. The container has a known fixed volume, and the measurement phase is used to determine the amount of milk which has been pumped into the container. In the measurement phase, air is pumped to/from the container, and the change in pressure and number of pump rotations, or time the pump is running for, along with the operation equation and known volume of empty container are used to determine the volume of liquid in the container.

The container is nominally a fixed volume. When pumped to pressure, the container sides may deform, changing the volume accordingly. This deformation can be characterised theoretically with Finite Element Analysis for example, or experimentally and a correction factor applied to the operational equation.

In some embodiments, once the volume of fluid in the container has been determined, the value is output at step 206. The output value may be output to a user, through transmitting the value to a processor and displaying it on a user interface. The user interface may be associated with an app on a mobile device.

Calibration Phase

FIG. 3 shows an example of the calibration phase according to some embodiments. The method 300 shows a method of deriving an operational equation in the calibration phase. The skilled person will understand that a number of specific implementations could fall under the method 300. For illustrative purposes, an example of specific steps of a method of calibration is given in FIG. 5. The skilled person will understand that the method is not limited by the specific measurements referred to in specific FIG. 5.

In some embodiments, a container is attached to the system 100. The container may be empty (i.e. except for air) and has a fixed known volume. For example, the container may be 100 ml, 80 ml, 60 ml, or any other conceivable size.

At step 302 the pump 104 is run to pump air from the container. At the beginning of the calibration phase, the container is at approximately atmospheric pressure. In some embodiments, the pump is a negative air pump, pumping air from the container to decrease the pressure in the container. In other embodiments, the pump may be a positive pressure pump to pump air into the container and increase pressure in the container. In some implements the pump is run to a threshold value, which will be discussed in detail below.

At step 304, measurements of the pressure in the container and the number of rotations of the pump are taken. In some embodiments, instead of measuring the number of rotations of the pump, the time the pump is running for is measured instead. These measurements are used, along with ideal gas law and the volume of the container, to calculate the amount of air which has been pumped during step 302.

The measurements are noted for use later in the method in determining an operation formula.

In some embodiments, at step 306, the container is changed for a container having a different, known fixed volume. The container volumes used may be 100 ml, 80 ml, 60 ml, or any other conceivable size.

Once the container has been changed, steps 302 to 304 are repeated with a new size of container. The pump is run at step 302. It may be run to a threshold value, described in more detail below. At step 304, measurements of the pressure in the container and the number of pump rotations (/time the pump is running for) are taken. In addition, ideal gas law and the volume of the container are used to calculate the amount of air which has been pumped from the container during the pumping in step 302. The amount of air may be the number of moles or the volume of the air.

Steps in the methods disclosed herein use ideal gas law. Ideal gas law $$PV = nRT$$

P=pressure
V=volume
n=amount of substance (number of moles)
R=ideal gas constant
T=temperature In the methods disclosed herein, the pressure may be measured by the pressure sensor 112. Temperature may be measured by a temperature sensor (not shown in FIG. 1) and the measured value is included in the calculations. The temperature sensor may measure the temperature inside the container, or may measure the temperature outside the container which is used as a guide for the temperature inside the container. Alternatively, a standard temperature may be used. For example, it might be decided that a standard operating temperature of 30 degrees will be used in the calculations. Other standard operating temperatures, for example between room temperature and body temperature, may be used. In some embodiments, the temperature is not taken into account in the calculations.

The container may be changed again for a different, known fixed size of container in step 306. Steps 302 to 304 are repeated for each new container size.

Once the steps have been performed on a number of containers, the values established in step 304 can be used to derive an operation equation for the pump 104 at step 308. To derive an operation equation, regression analysis is used.

To derive an operation equation for the pump, analysis is performed on the measurements recorded in step 304.

In some embodiments, a line of best fit is derived on the data values using regression analysis. For example, the Least Squares Method may be performed on the data to determine a line of best fit to the data to derive an operation equation. In implementations this is performed on a processor in the controller. Alternatively the data points are sent to an external processor where the analysis is performed.

In other embodiments, the measurements taken in step 304 may be plotted on a graph and the line of best fit can be used to find a gradient and a point of interception to form an operation equation. The x and y values of the operation equation will depend on the values plotted on the graph, and on the measurements taken.

The operation equation will link any of the change in pressure, the number of pump rotations and the amount (volume or moles) of air pumped from the container.

In some embodiments, at step 310 the operation equation is outputted for use. The operation equation is specific to the pump 102 which the calibration phase has been run on. The operation equation is outputted for use in measuring the amount of milk in a container using the pump used in the calibration phase. The operation equation may be outputted to the pump controller, or to a processor or memory.

Measurement Phase

Figure 4:
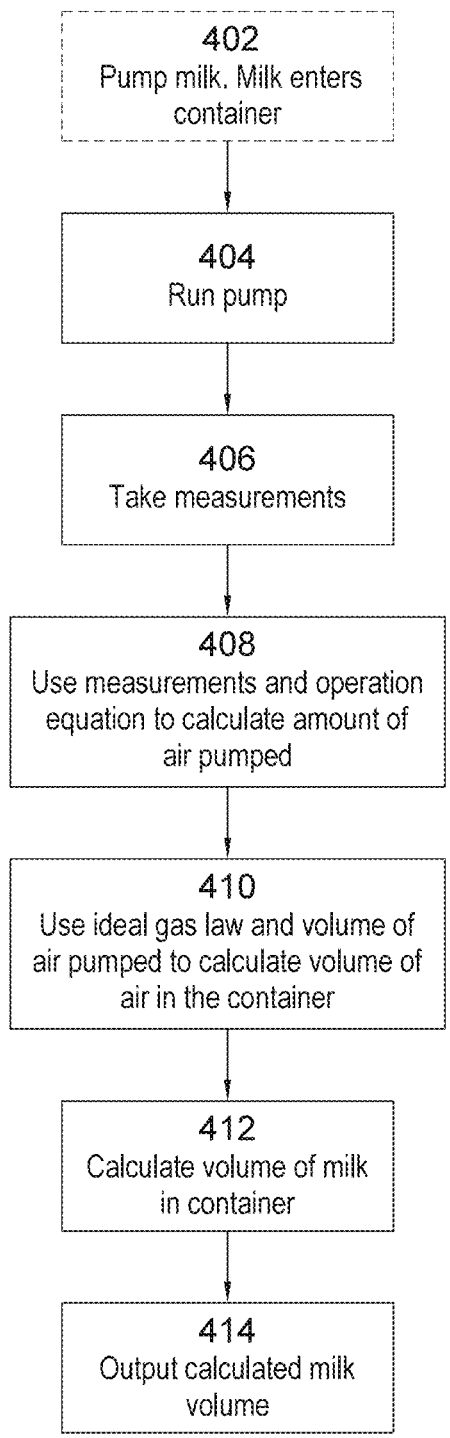
FIG. 4 shows a measurement phase according to an embodiment of the invention.

The measurement phase according to some embodiments is shown in FIG. 4. The measurement phase uses the operation equation to determine the volume of milk in the container.

The measurement phase happens at the start of a pumping session of a user to determine if the bottle attached to the breast pump is empty, during a pumping session of a user to determine the progress towards the user's milk volume target, or at the end of a pumping session of the user to determine their final volume of milk pumped. The measurement phase can be used to determine if the bottle is full, in which case an output is given indicating that an ongoing session should pause.

The container in the pumping session is a container of fixed known volume. In some embodiments, the breast pump system in which the measurement system is configured to fit in a user's bra. Therefore, the container 102 may be shaped with an external convex shape to align with the contouring of a woman's breast when placed in a bra during use.

In mass production, it is likely the container volume will exhibit some variation as a result of manufacturing tolerances. Therefore, there will be an associated tolerance to the known volume, and this will directly impact the accuracy of liquid measurement. In some embodiments, the manufactured volume of the container could be measured in the factory or elsewhere and the volume modified with a subsequent manufacturing process or part. In other embodiments, the manufactured volume of container could be measured in the factory or elsewhere and that information stored in a way that's accessible to the breast pump, for instance using RFID tags, optical bar codes or simply plain text (so that the user can communicate over a user interface the actual size of cavity). These steps would improve the accuracy of liquid measurement.

In some embodiments, before the measurement phase, at step 402, the breast pump is activated and milk is pumped from the user's breast. As explained above, pumping pressure is generated at the user's nipple and milk is expressed into a nipple tunnel of the breast shield. Milk then flows along the milk path and into the container 102. The pump used to generate the pumping pressure may be pump 104, or may be a separate pump.

In some embodiments, the measurement phase begins at 404 by running the pump 104 to remove air from the container 102. The pump may be run to a threshold value, and this may be the same threshold value used in the calibration phase. Details of this are given below in example 1.

In some embodiments, once the pump has been run, measurements of the pressure in the container and the number of pump oscillations, for example as measured with the encoder, or time of the pump running using a timer, are taken at step 406.

The measurements can be then used along with the operation equation to calculate the volume of milk in the container.

In some embodiments, at step 408 the measurements are used and inputted into the operation equation to calculate the amount of air pumped out during step 404 of the measurement phase. At step 410 the amount calculated is used with the ideal gas law to calculate the amount of air left in the container. The volume of the container and the amount of air left in the container is used to calculate the volume of milk in the container.

In some embodiments, the method may differ from the specific method shown in FIG. 4 and ideal gas law is not used. An operation equation based on the number of rotations required to read a threshold bottle pressure for different sized bottles is used. The number of pump oscillations required to pump the container to a threshold pressure is measured. The measured number of oscillations is input to the operation equation to determine the volume of air in the container. The volume of milk in the container can be determined using the difference between the total container volume and the volume of air in the container. Therefore the method need not necessarily rely on ideal gas law. However, including ideal gas law in calculations can provide certain benefits, such as increased accuracy of the milk volume measurement. It is therefore clear that not all of the steps in FIG. 4 are essential, and the measurements taken in step 406 can be used in a number of ways to calculate the volume of milk in the container, not specifically limited to steps 408 and 410.

Finally, in some embodiments, at step 414 the calculated volume of milk is outputted, as in step 206.

It may be determined, based on the calculated volume of milk, that the milk container is full or nearly full. The calculated volume of milk, calculated in step 412 may be compared to the known volume of the bottle. If the calculated volume of milk is within a threshold amount of the container volume, for example within 5 ml or 10 ml of the container volume, then it may be determined that the bottle is full.

The volume of air in the container calculated in step 410 may also be used to determine whether the milk bottle is full. For example, if the volume of air in the container is less than a threshold amount, such as 5 ml or 10 ml, then it may be determined that the milk bottle is full.

In some embodiments, on determining that the bottle is full the controller sends a signal to a user to indicate that the bottle is full, and/or sends a signal to pause the pumping session. The user may then empty the container, or attach another container, and resume the pumping session.

Examples of methods of FIGS. 3 and 4 are given in FIG. 5.

Example 1

The following steps are steps taken in a specific example of a calibration and measurement method.

In example 1, at step 302 the pump 104 is run to a threshold pressure in the container 102. This is the ideal threshold pressure in the container for normal use of the container. In a breast pump, the threshold pressure may be the pressure for creating a suitable vacuum in the container in order to generate a base level vacuum. The threshold pressure may be, for example −50 mmHg (gauge, from atmospheric pressure). Of course, −50 mmHg gauge pressure is the same as 710 mmHg absolute pressure when the atmospheric pressure is 760 mmHg. The pressure is measured by the pressure sensor 112. The pump 104 pumps air from the container 102, reducing the pressure in the container. When the pressure sensor signals that the threshold pressure value has been met, the controller stops the pump from pumping.

The pump sensor counts the number of pump oscillations required by the pump in step 302 to reach the threshold pressure. For example, for a rotary pump the rotary encoder 108 counts the number of pump rotations. At step 304, this measurement is noted or recorded.

Next, the volume of air pumped out during step 302 is calculated. This is done using ideal gas law, for example:

a. Calculate moles pumped out to reach threshold pressure in step 302

$$\text{Moles pumped out} = \text{Moles of gas in volume}_{atmos} - \text{Moles of gas in volume}_{threshold}$$

Where, using ideal gas law:

$$\text{Moles of gas in volume}_{atmos} = \frac{\text{atmospheric pressure} \times \text{volume of calibration volume}}{\text{molar gas constant} \times \text{temperature}}$$

$$\text{Moles of gas in volume}_{threshold} = \frac{\text{threshold pressure} \times \text{volume of calibration volume}}{\text{molar gas constant} \times \text{temperature}}$$

a. b. Calculate the volume pumped out

1. $$\text{Volume pumped out} = \frac{\text{moles pumped out} \times \text{molar constant} \times \text{temperature}}{\text{atmospheric pressure}}$$

The two values which have been determined: the volume of air pumped out during step 302 and the number of pump rotations during step 302 may be noted, recorded or stored.

Steps 302 to 304 are repeated for any number of containers, from two to five or more. For each container, the pump is run to a threshold pressure, the number of pump oscillations are counted, the volume of air pumped is calculated, and these two latter values are noted.

After these steps have been repeated for a number of container sizes, a line of best fit can be determined by the noted values and measurements. For example the values/measurements from steps 302 and 304 may be plotted on a graph with, for example, air volume pumped out on the y axis, and number of pump oscillations on the x axis. The line of best fit is used to derive the operating equation. The line of best fit typically has a gradient and a y-axis intercept.

$$\text{Air volume pumped out} = m \times \text{oscillations count} + c$$

Where:

m=gradient of line c=y axis intercept

The y intercept will be zero, since zero pump rotations will pump zero air.

In other examples, the measurements are not plotted on a graph but rather a regression analysis is performed on the values to determine an operation equation. A regression analysis, such as Least Squares Method is performed on the values of volume of air pumped out and the number of pump oscillations recorded from steps 302 and 304 to determine an operation equation in the form:

$$\text{Air volume pumped out} = m \times \text{oscillations count} + c$$

Other forms of analysis may be used on the recorded measurements to determine an operation equation.

The operation equation is then outputted. The calibration method may be performed by the processor in the controller.

In the measurement phase of example 1, the user operates the breast pump to pump milk into the container 102 at step 402.

When fluid flows into the container 102 the vacuum pressure in the container decreases. Optionally, once fluid (milk and/or air) is pumped into the container at step 402, before step 404, container vacuum pressure is further decreased to atmospheric pressure or part-way to atmospheric pressure using the pump configured to pump air into the container or through a bleed valve. This is beneficial as an increased difference from the threshold pressure target increases accuracy during step 404 due to an improved signal to noise ratio.

At step 404, the pump is run to the threshold pressure in the container. The threshold pressure is the same value of threshold pressure used in the calibration phase. The threshold pressure may be, for example 50 mmHg. The pressure is measured by the pressure sensor 112. The pump 104 pumps air from the container 102, reducing the pressure in the container. When the pressure sensor signals that the threshold pressure value has been met, the controller stops the pump from pumping.

The pump sensor counts the number of pump oscillations required by the pump in step 404 to reach the threshold pressure. For example the rotary encoder 105 counts the number of pump rotations. At step 406, this measurement is noted or recorded.

Next at step 408 the operation equation and the recorded number of pump rotations is used to determine the volume of air pumped out during the measurement phase (i.e. during step 404).

This is done by:

$$\text{Volume pumped out} = m \times \text{number of oscillations} + c$$

Where m and c are the values determined in the operation equation.

At step 410, ideal gas law is used to calculate the volume of air left in the container in the calibration phase. This is done using the following equations:

$$\Delta n = \frac{P_{atmos} \times V}{R \times T}$$

Where:
- Δn=member of moles pumped out
- $P_{atmos}$=atmospheric pressure
- V=volume pumped out (calculated in step 408)
- R=ideal gas constant
- T=temperature Once the number of moles pumped out has been determined, this can be used to calculate the volume of air in the container:

$$V_{air} = \frac{\Delta n \times R \times T}{P_{atmos} - P_{threshold}}$$

Where
$V_{air}$ is the volume of air in the container.

Finally, the volume of milk in the container is calculated, $$V_{milk} = V_{container} - V_{air}$$

Where
$V_{milk}$ is the volume of milk
$V_{container}$ is the known fixed volume of the container.

The volume of milk is outputted at step 414.

Throughout the calibration and measurement methods, when air is pumped from the containers to achieve a threshold pressure, once the data has been taken and before the pumping session is resumed, the pressure in the milk container is returned to a base level vacuum pressure.

Example 2

A different example is also provided as follows.

In example 2, at step 302 the pump 104 is run to a threshold number of rotations. The threshold number of rotations may be, for example, 100, 150 or 200 rotations. The number of oscillations is counted by the pump sensor 105. The pump 104 pumps air from the container 102, reducing the pressure in the container. When the encoder signals that the number of rotations is equal to the threshold number, the controller stops the pump from pumping.

The pressure in the container after the threshold number of pumps is measured in step 304. The pressure is measured by the pressure sensor 112.

Next, the volume of air pumped out during step 302 is calculated. This is done using ideal gas law.

Next, at step 304, the two values which have been determined: the volume of air pumped out during step 302 and the pressure in the container after the threshold number of oscillations are recorded.

Steps 302 to 304 are repeated for any number of containers, from two to five or more. For each container, the pump is run to a threshold number of oscillations, the pressure is measured, the volume pumped is calculated, and these two latter values are recorded.

After these steps have been repeated for a number of container sizes, an operation equation can be determined using regressions analysis. This may be a line of best fit on a graph, or may be another type of regressions analysis, for example Least Squares Method on the values.

$$\text{Volume pumped out} = m \times \text{pressure}$$

m=derived coefficient

The operation equation is then outputted. The calibration method may be performed by the processor in the controller.

In the measurement phase of example 2, the user operates the breast pump to pump milk into the container 102 at step 402.

At step 404, the pump is run a threshold number of oscillations. The threshold number of oscillations is the same value of the threshold number of oscillations used in the calibration phase. The threshold number may be, for example 100, 150 or 200 oscillations. The number of oscillations is measured by the pump sensor. The pump 104 pumps air from the container 102, reducing the pressure in the container. When the sensor count reaches the threshold number, the controller stops the pump from pumping.

The pressure in the container after the threshold number of oscillations is measured in step 406. The pressure is measured by the pressure sensor 112.

Next at step 408 the operation equation and the measured pressure is used to determine the volume of air pumped out during the measurement phase (i.e. during step 404).

This is done by:

$$\text{Volume pumped out} = m \times \text{measured pressure}$$

Where m is the value determined in the operation equation.

At step 410, ideal gas law is used to calculate the volume of air left in the container in the calibration phase. This is done using the following equations:

$$\Delta n = \frac{P_{atmos} \times V}{R \times T}$$

Where:
- Δn=member of moles pumped out
- $P_{atmos}$=atmospheric pressure
- V=volume pumped out (calculated in step 408)
- R=ideal gas constant
- T=temperature Once the number of moles pumped out has been determined, this can be used to calculate the volume of air in the container:

$$V_{air} = \frac{\Delta n \times R \times T}{P_{atmos} - P_{measured}}$$

Where $V_{air}$ is the volume of air in the container.

Finally, the volume of milk in the container is calculated:

$$V_{milk} = V_{container} - V_{air}$$

Where $V_{milk}$ is the volume of milk $V_{container}$ is the known fixed volume of the container.

The volume of milk is outputted at step 414.

The method in example 2 may be beneficial since a high-resolution encoder to measure the number of pump oscillations is not required.

The disclosed embodiment relates to manipulating variables in ideal gas law to determine the volume of gas in a known volume container (and therefore determine the amount of liquid).

Ideal gas law is described above, and includes variables PV=nRT. There are a number of variables to manipulate to determine the volume of gas. Therefore the disclosure includes a number of options to obtain the desired measurement. Each option relies on manipulating/measuring two different variables to determine the amount of gas in the container. The variables which are not manipulated/varied are assumed to be constant throughout the methods.

Example 3

In example 3, (not shown in the figures) there is no calibration phase. There is no need for a rotary encoder on the pump in example 3, since the volume of air pumped by air pump is not determined using the number of pump rotations but instead using an external flow rate sensor.

In the measurement phase of example 3, the user operates the breast pump to pump milk into the container 102 at step 402.

When fluid flows into the container 102 the vacuum pressure in the container decreases. Optionally, once fluid (milk and/or air) is pumped into the container at step 402, before step 404, container vacuum pressure is further decreased to atmospheric pressure or part-way to atmospheric pressure using the pump configured to pump air into the container or through a bleed valve. This is beneficial as an increased difference from the threshold pressure target increases accuracy during step 404 due to an improved signal to noise ratio.

At step 404, the pump is run to a threshold pressure in the container. The threshold pressure may be, for example 50 mmHg. The pressure is measured by the pressure sensor 112. The pump 104 pumps air from the container 102, reducing the pressure in the container. When the pressure sensor signals that the threshold pressure value has been met, the controller stops the pump from pumping.

At step 408 an external flow rate sensor outside the pump is used to measure the volume of air which flows through the pump during step 404. (i.e. measuring the volume of air pumped by the pump). In this step, the external flow rate sensor senses the amount of air flowing past or through the sensor, and uses an equation to determine the volume of air pumped based on the measured flow rate.

Steps 410-414 are performed using the equations above in example 1.

In a variation of example 3, the pump may be run to a threshold volume of air pumped. The pump is run and the external flow rate sensor measures the volume of air pumped by the pump. Once a threshold volume of air has been pumped (as determined by the flow rate sensor) the pumping stops. The pressure in the milk container is then measured. The equations in example 2 are used to calculate the volume of milk.

Example 4

In example 4 (not shown in the figures), the time the pump is running for is used to measure the amount of air which is pumped into or from the container. The method follows that similar to example 1 or example 2. In a method similar to example 1, the pump is run to a threshold pressure at 302 and the time it takes for the pump to reach the threshold pressure is measured at 304. The volume of air pumped out is derived, and an operation equation relating the time of operation of the pump to the volume of air pumped out is derived at 310. In the measurement phase the pump is run to the threshold pressure at 404 and the time taken for the threshold pressure to be achieved is measured at 406. The operation equation is used to calculate the volume of air pumped out using the measured time of operation of the pump. Ideal gas law is used to calculate the volume of air in the container at 410, and the volume of milk is calculated at step 412. That is, measuring the number of pump oscillations in example 1 can be replaced by measuring the length of time the pump is run for, and the method steps/calculations are updated accordingly. The relationship between the volume of air pumped and the operation time of the pump is derived in the calibration phase, and used in the measurement phase.

In a method similar to example 2, the pump is run for a threshold amount of time (for example, 5 seconds) and the resulting pressure after the threshold amount of time is measured. The pump is run for a threshold amount of time at 302 and the pressure in the container after the threshold amount of time is measured at 304. The volume of air pumped out is derived using ideal gas law, and an operation equation relating the time of operation of the pump to the volume of air pumped out is derived at 310. In the measurement phase the pump is run for the threshold amount of time at 404 and the pressure in the container after the threshold amount of time is measured at 406. The operation equation is used to calculate the volume of air pumped out using the measured pressure. Ideal gas law is used to calculate the volume of air in the container at 410, and the volume of milk is calculated at step 412. The relationship between the change in pressure over the pump operation time is derived in the calibration phase, and used in the measurement phase. That is, the threshold number of pump rotations in example 2 is replaced by a threshold amount of time that the pump is run for, and the method steps/calculations are updated accordingly.

The above examples have involved manipulating two variables (pressure and volume) to determine the amount of fluid in a container.

Option A: The variables are P and n.

FIGS. 3 and 4 describe a method which changes the pressure by a set amount in a container and measures the amount of gas required to achieve the change in pressure (example 1) or changes the amount of gas in a container by a set amount (number of moles) and measures the change in pressure (example 2).

Of the variables in ideal gas law, therefore, the method described in FIGS. 3 and 4 manipulate pressure P and amount of gas n.

Option B: Change the volume of the container by a known amount and monitor the associated change in pressure or temperature. The variables relied upon are V and P or T.

Some means of increasing or reducing the volume of the container by a known amount will result in a pressure change inside the sealed container. For example, an internal bladder in the container could be inflated to a known volume. By measuring the associated pressure change, or temperature change, the air volume of the container can be calculated. The liquid volume can be calculated by subtracting the air volume from the known container volume.

Some examples of ways to increase/reduce the volume of the container include:

Incorporate a piston into the bottle, which can be extended, or retracted by a known distance. This known distance means we can calculate the air volume that has changed.

Option C: Connect the container to another container of known volume at a different pressure to the first container (changing both the container volume and quantity of gas by known amounts). The variables relied upon are n, V, and P.

The liquid container with attached pressure sensor can be pumped to a known pressure above or below atmospheric pressure. A second sealed container at a different known pressure, can be connected to the liquid container using a valve, changing both the container volume and quantity of gas in the combined container by known amounts. The air volume can be calculated using the associated pressure change. The liquid volume can be calculated by subtracting the air volume from the combined container volume.

Option D: Pump the container up to a known pressure and subsequently bleeding air to or from the container through a known orifice diameter. The variables relied on are P and n.

The liquid container is pumped to a known pressure and subsequently bled with a valve through an orifice hole of a fixed diameter.

A calibration phase is conducted by measuring the time taken for the liquid container pressure to revert to atmospheric pressure. Using regression analysis, an operational equation is derived by correlating the measured time period to the quantity of gas added to the container.

When conducting a measurement, the time to revert to atmospheric pressure can be measured, and using the operational equation the quantity of gas added to the container is calculated. This can then be used to calculate the volume of air in the container using ideal gas law.

The pump can be used to remove gas from the container and reduce the pressure. During measurement, air is bled into the container to increase the pressure and return the container to atmospheric pressure. In an alternative embodiment, the pump is used to pump gas into the container to increase the pressure. During measurement air is bled from the container to reduce the pressure and return the container to atmospheric pressure.

Option E: Add liquid to a container of a known volume. Using Boyle's law, calculate the new air volume from the pressure change. The v relied on are V and P.

The following idea does not need a pump for the idea to work—it only needs a pressure sensor attached to the bottle. As milk is added to the bottle, the pressure will rise. This means the new air volume inside the container can be calculated from the pressure change using Boyle's law.

Boyle's law states that the absolute pressure exerted by a given mass of an ideal gas is inversely proportional to the volume it occupies if the temperature and amount of gas remain unchanged within a closed system.

This idea works when the following is true: we know the air volume of the container at the start of a pumping session and the bottle is sealed without any significant air leaks.

In the event there is a leak in the bottle, it is possible to calculate the leak rate by observing the pressure change over time during the periods that the NRV is sensed to be closed (by comparing pressure in nipple tunnel vs bottle). This averaged leak rate can be used to correct for leaks inside the bottle during a milk measurement.

A further way to measure leak rate is to use Option E in conjunction with one of the other techniques (Options A-D). Option A-D typically take very little time (0.5-1 second is typical) to measure the liquid volume, and so the effect of air leak on these measurements is expected to be negligible. Therefore, it is feasible to use Option E as the primary liquid measurement method (which is susceptible to accumulating errors due to air leaks), and periodically use one of the Options A-D to correct any error caused by an air leak.

Subsequently it is feasible to calculate the average air leak by comparing the two liquid volume estimates. Once compared, the average air leak can be factored into the Option E measurement to increase the accuracy of Option E measurements and reduce the frequency of corrective Option A-D measurements.

Figure 6:
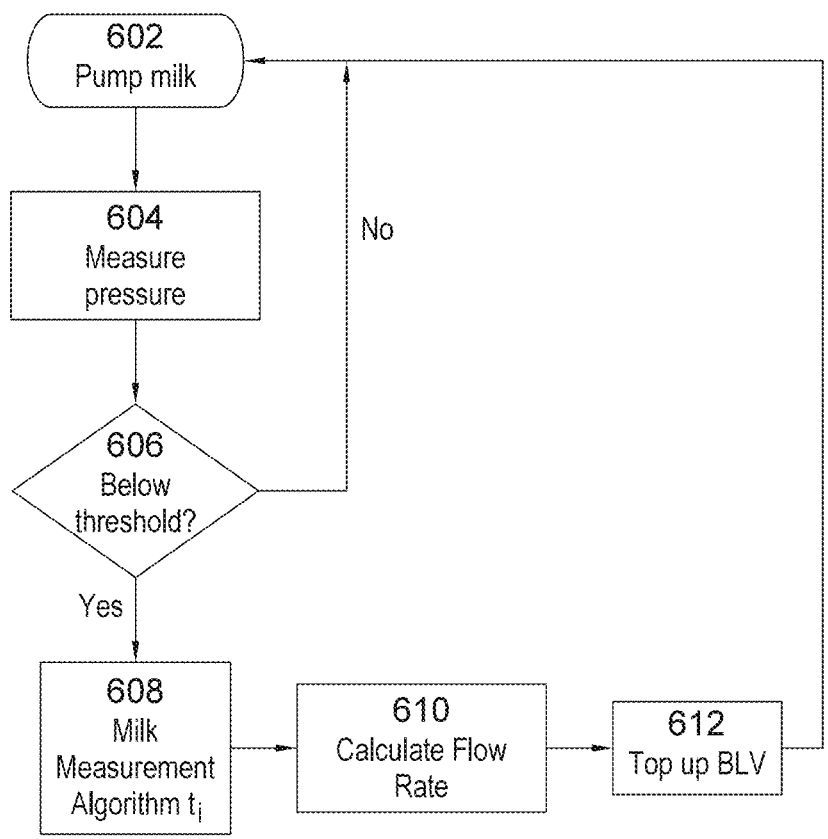
FIG. 6 shows milk measurement during a pumping cycle.

FIG. 6 illustrates how the disclosed measurement method can be used during a pumping session to determine the flow rate of milk.

Essentially, the volume of milk can be determined at two separate points in time, and used in a flow rate algorithm to determine the flow rate.

The flow rate algorithm is:

$$\text{Flow rate} = \frac{V_{t2} - V_{t1}}{\Delta t}$$

Where:
$V_{t1}$=Volume of milk at time 1 (time 1 being the time the first measurement was taken)
$V_{t2}$=Volume of milk at time 2 (time 2 being the time the second measurement was taken)
$\Delta t$=change in time=$t_2-t_1$ Knowing the flow rate can be useful to a user to provide information on which pumping sessions produce more milk, and on how much milk the current session is producing. It is useful for a user to know which pumping cycles have the highest flow rate, and whether there are certain points within a pumping cycle which have a different, for example a higher or lower, flow rate, and to switch between pumping profiles when a certain flow rate has been reached. For example, the information may be used to switch from a stimulation mode of the breast pump to an expression mode. Stimulation mode is typically used to replicate the early stages of an infant suckling a breast to encourage milk production. Expression mode is typically used with the main focus of extracting milk as efficiently as possible once milk production has started.

In certain breast pumps, including the breast pump disclosed in embodiments herein, a base level vacuum is maintained throughout the system, including in the breast shield and the container. The base level vacuum is a negative pressure (pressure less than atmospheric pressure) which ensures the breast shield stays fitted to and sealed against the mother's breast.

The base level vacuum is maintained by a pump (which may or may not be the same as the pump 104 of the measurement system). When the system is sealed, the pressure in the same system will stay constant unless fluid is introduced to or removed from the system. Assuming no air is pumped into or out of the system, and that there are no leaks, the only way this will happen is when milk is introduced from the user's breast.

When milk enters the system from the user's breast, the volume of total fluid in the system increases, and therefore the vacuum reduces (i.e. the absolute pressure increases). This is referred to as the vacuum in the container 'dropping below' a threshold.

When milk is introduced to the system the pressure increases, and therefore there is a weaker vacuum pressure holding the pump onto the user's breast.

The milk flows from the nipple along the milk path to the container. Therefore the absolute pressure in the container increases/the vacuum pressure reduces. The pressure sensor 112 can be used to detect the pressure in the container to indicate when the pressure increases as a result of the volume of milk in the container.

During milk measurement the breast pump cannot be used to pump breast milk, and therefore it is desirable to minimise the frequency of milk measurements to avoid interrupting the pumping session. It is also desirable to measure the volume of milk frequently enough to obtain accurate and relevant flow rate information. Therefore a balance between measuring frequently enough to provide useful information, not so frequent as to negatively impact the user, should be found. One way to determine when the volume of milk should be measured is to use the pressure in the container.

As milk and air are pumped into the container, the pressure increases. The pressure in the container can be measured to determine when the vacuum drops below a certain threshold. A drop in vacuum indicates that fluid has been pumped into the container. A large drop in vacuum indicates that a large amount of fluid has been pumped. A small drop in vacuum indicates that a small amount of fluid has been pumped. A threshold can be chosen, such that if the vacuum pressure drops below the threshold it indicates that enough milk has been pumped that it is worth measuring the volume of milk. This measurement can be used to provide an updated milk flow rate as indicated in the method in FIG. 6.

In some embodiments, at step 602 milk is pumped from the user.

In some embodiments, at step 604 the pressure in the container 102 is measured using the pressure sensor 112. In some embodiments, at step 606, the measured pressure is compared to a threshold. If the pressure is below a threshold value, then the process returns to step 602 and pumping continues. If the pressure is above a threshold value, meaning there is a less strong vacuum pressure in the system, then the method continues to step 608. The pressure in the container being above a threshold value indicates that fluid has entered the system, and that it would be beneficial to measure the volume of milk in the container.

The pressure in the container can be measured whilst milk is being pumped. The pressure sensing in step 604 can happen concurrent with pumping milk in step 602. In some embodiments, at step 608 the milk measurement method, such as that shown in FIG. 4, is performed at a specific time, to determine the volume of milk in the container at that time.

In some embodiments, once the volume of milk has been determined, the measured volume is used in the flow rate algorithm, along with a previous measure of the volume at the previous measurement time ($t_{i-1}$), to calculate the flow rate at step 610. The flow rate between time i and time i−1 is calculated using the above flow rate algorithm.

In some embodiments, once the flow rate has been calculated at step 610, pumping milk at step 602 resumes. The flow rate calculated in step 610 may be used to switch between pumping profiles. Therefore, when the method returns to step 602 following step 610, the pumping profile (force, frequency) may be different to the pumping profile used at the start of the method.

At any point in the pumping cycle, when the pressure increases such that the vacuum drops below a threshold value, such as −35 mmHg (appropriate if the desired base level vacuum is −50 mmHg), the base level vacuum can be "topped up" to ensure at least a minimum negative pressure is maintained to ensure a consistent seal between the breast shield and the user's breast.

The process in FIG. 6 can happen between cycles, at multiple times in a pumping session, to provide an updated flow rate measurement to the user and to ensure the base level vacuum is always maintained at least a threshold value.

Figure 7:
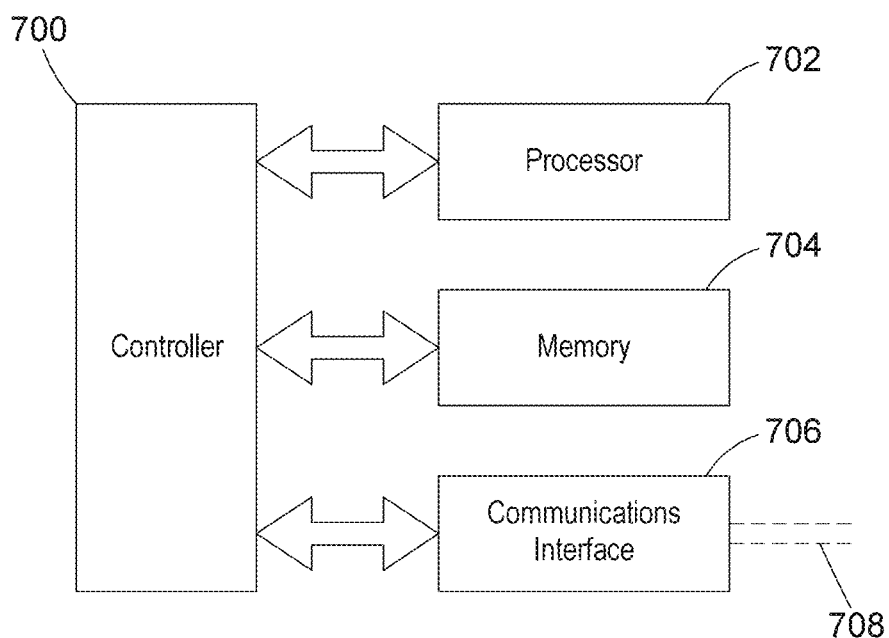
FIG. 7 shows a schematic drawing of a controller according to an embodiment of the invention.

FIG. 7 shows a schematic diagram of a controller according to some embodiments. The controller 700 may be configured to control the pump and/or perform the calculations according to the methods disclosed herein.

The controller 700 may comprise a processor 702 configured to perform the method disclosed herein.

The controller 700 may also comprise a memory 704 having computer-executable instructions which, when executed by processor 702, cause the processor to implement the methods disclosed herein.

The memory 704 may also store data obtained during the methods. The memory may be transitory or non-transitory.

The controller 700 may also comprise a communication interface 706 for sending and/or receiving data via a communications channel 708. The data may be sent wirelessly, for example using a wireless transceiver. The data may be sent via a wireless connection, for example via Bluetooth or WiFi. The data may be sent to a remote wireless device, for example a user device such as a smartphone, a tablet device or a computer. The remote wireless device may comprise a display interface to display information to the user about the milk measurement method and data disclosed herein.

Altitude Compensation

Some measurement systems and methods described herein relate to running the pump to a threshold pressure at step 302 and/or step 404, such as in example 1 in FIG. 5. When testing such systems and methods at a simulated altitude above sea level (after calibration at sea level), the altitude was found to be responsible for an error. This is because the decreased density of the air at altitude is resulting in the pump requiring more pump cycles to pump to the threshold pressure. This means, when at altitude, the system might overestimate the air volume in the bottle and therefore underestimate the milk volume in the bottle.

In some embodiments, therefore, it is provided that the measurement system and methods include an altitude compensation. The altitude compensation may involve making the threshold pressure used during calibration and measurement changes dependent on the atmospheric pressure. One example is depicted in FIG. 8.

Figure 8:
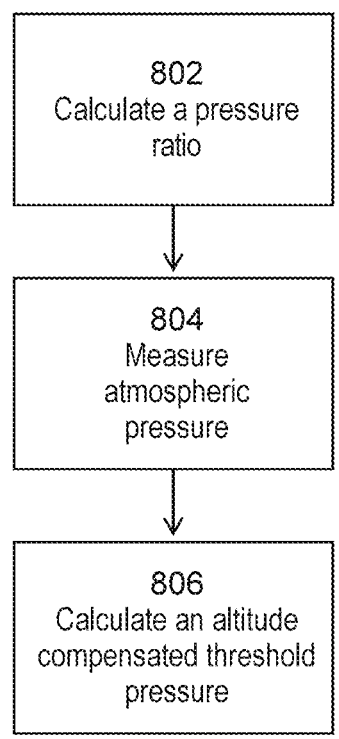
FIG. 8 shows an altitude compensation method.

FIG. 8 depicts an altitude compensation method 800. The method 800 takes the threshold pressure (the same threshold pressure as described above) and outputs an altitude compensated threshold pressure.

In some embodiments, a first step 802 is to calculate a fixed pressure ratio. The fixed pressure ratio can be calculated using this equation:

$$\text{Pressure Ratio} = \frac{\text{Threshold Pressure}}{\text{Standard Atmospheric Pressure}}$$

The threshold pressure is the same threshold pressure as described herein. That is, it is the threshold pressure in the container for normal use of the container. In a breast pump, the threshold pressure may be the pressure for creating a suitable vacuum in the container in order to generate a constant vacuum at the breast. For example, in a breast pump the target pressure for creating a vacuum in the container may be 710 mmHg (absolute), when the atmospheric pressure is 760 mmHg. Of course, any suitable absolute target pressure may be used, depending on the system of the container. For use in the equation, the threshold pressure should be an absolute value. It is absolute in that it is the pressure as compared to a perfect vacuum rather than as compared to standard atmospheric pressure (gauge pressure). Standard atmospheric pressure may be the pressure of the average atmospheric pressure at sea level. The standard atmospheric pressure may be 1 atm or 760 mmHg.

This pressure ratio calculation may be calculated at any time, it does not need to be done immediately prior to the milk calibration phase and/or measurement phase. This pressure ratio may be considered "fixed" as it can be fixed prior to use of the container and not re-calculated.

In some embodiments, a next step 804 is to measure atmospheric pressure. A pressure sensor can be used to measure the pressure external to the container. This measurement is taken immediately prior to the milk calibration phase and/or measurement phase.

In some embodiments, a next step 806 is to calculate an altitude compensated threshold pressure. The altitude compensated threshold pressure is calculated using:

Altitude Compensated Threshold Pressure =

Measured Atmospheric Pressure * Pressure Ratio

The measured atmospheric pressure is the atmospheric pressure measured at step 804. The pressure ratio is the pressure ratio calculated at step 802. The threshold pressure will be an absolute pressure (i.e. not the pressure compared to atmosphere).

The altitude compensated threshold pressure calculated in step 806 can then be used in the methods described herein in place of the threshold pressure. For example, the altitude compensated threshold pressure can be used instead of the threshold pressure at steps 302, 404 and in example 1 of FIG. 5.

Method 800 allows for the present measurement systems and methods to be used anywhere around the world at different altitudes since altitude induced errors are significantly reduced.

Diaphragm Stiffness

As shown in FIG. 1, there may be a flexible diaphragm 106 within the milk container 102 or outside of the milk container. Flexible diaphragms may have a stiffness which is not a fixed value, rather it might have a variable stiffness profile. A stiffness profile is force vs displacement. The stiffness profile of the flexible diaphragm might be non-linear. This is a problem because if a flexible diaphragm with a variable stiffness profile is replaced by a new flexible diaphragm also with a variable stiffness profile, it is highly likely that the two profiles of the old and new diaphragms will not match. This will impact the rate of pressure increase in the container and therefore how long it takes to reach the pressure threshold. Therefore, it can impact the measurement methods described herein.

For optimum accuracy of the methods herein, a flexible diaphragm 106 with a flat stiffness profile can be used, i.e. the displacement of the diaphragm does not change the force.

Alternatively, a flexible diaphragm with a linear increasing stiffness profile can be used. In this case a stiffness profile with a small gradient will be preferred over a large gradient. A suitable diaphragm stiffness profile for a circular diaphragm of 50 mm diameter may be one that increases linearly from 0 newtons at 0 mm of diaphragm movement, to 10 newtons at 15 mm diaphragm movement.

A flexible diaphragm with a non-linear stiffness profile is to be avoided, as this introduces error into the milk measurement system.

Venting

Another problem that may be solved using the measurement methods and system of the present disclosure is maximising the milk volume of the milk container 102 using an air venting process, in the context of breast pumps.

With reference to FIG. 1, the milk container 102 may have a flexible diaphragm 106 inside the milk container. One side of the diaphragm defines a wet side and the other side of the diaphragm defines a dry side. The milk is contained only in the wet side of the milk container 102 and not the dry side. The air pump 104 removes air from the dry side of the milk container 102. The air pump 104 is connected to the dry side of the milk container via an air path.

With the flexible diaphragm 106 inside the milk container, the volume of the wet side of the milk container will start at zero (or close to zero) and then gain volume as milk fills the wet side of the container. In an ideal scenario, when a pumping session is complete the volume of the wet side is full of milk. Therefore, the total volume of the wet side is equal to the total volume of milk collected. In reality, the wet side will contain some air as well as milk. Air inside the wet side of the milk container is undesirable because it takes up valuable space which could instead be filled with milk. In other words, air in the wet side of the milk container reduces the capacity of the milk container. This is inconvenient for the user since it reduces the amount of milk which can be pumped during one session or requires the milk container to be larger and therefore less discreet in bra. Even for milk containers where the wet side does not start at zero volume, and therefore contains air at the beginning of the session, the ability to minimise the amount of air in the bottle over the course of the session is still beneficial for improving milk capacity.

Air may be present in the wet side of the milk container for various reasons. Air may be present at the outset, when the milk container is empty of milk. Air may be drawn into the milk container when the breast pump starts pumping at the start of a session, before the milk has had a chance to flow from the user's breast. Most crucially, air may be drawn into the wet side of the milk container due to seal leaks. Any seal between the wet side of the milk container or parts of the breast pump to the atmosphere may let in air. For example, the breast shield is sealed to the breast, however, a non-perfect seal causes air to enter into the breast pump and milk container. Seal leaks are more likely to occur if the user is moving around whilst using the breast pump and interfering with the seal position of the breast shield on the breast.

Unwanted air in the milk container may be described as excess air. In some examples, a small amount of air present in the milk container may be desirable for the function of the breast pump. However, additional air over this small amount of desirable air is excess air.

The solution to these problems is to vent out the excess air from the wet side of the milk container either at the end of a pumping session, or even while the breast pump is in use. In other words, venting is the process of removing excess air contained in the milk container. This venting process allows more milk to be collected in the milk container, allowing the milk container to perform to its full capacity. This may be achieved using the measurement methods and system of the present disclosure.

Figure 9:
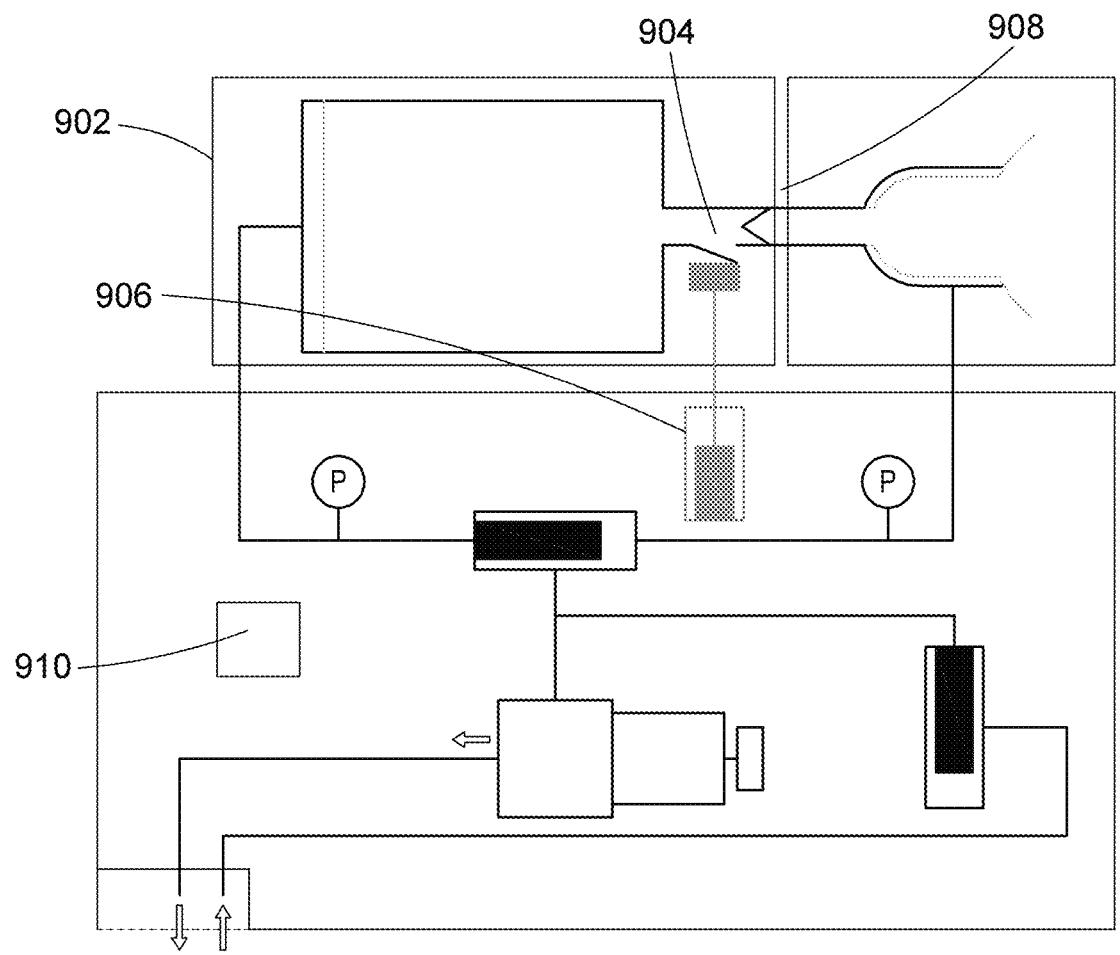
FIG. 9 shows a venting system according to an embodiment of the invention.

Reference will now be made to FIG. 9.

FIG. 9 depicts a milk container 902 according to the some embodiments. The milk container 902 may comprise means for venting air. The means for venting air may comprise a valve 904 located on the wet side of the milk container and an actuator 906 configured to open the valve.

The valve 904 may be of any suitable type. One example valve is depicted in FIGS. 5A and 5B. The valve 904 is located such that when the valve is open the wet side of the milk container is open to the atmosphere. In some embodiments, the valve 404 is located near the non-return valve 908 which is near the entrance to the milk container. In some other embodiments, the valve 904 is located in the body of the milk container 902.

In some embodiments, the milk container 902 may comprise means for detecting the orientation 910 of the milk container. The means for detecting the orientation 910 of the milk container may be any suitable means. For example, an accelerometer, electronic gyroscope and/or an IR system. The IR system may comprise an IR transmitter and receiver, both located inside the milk container. At certain orientations, the milk will block or interfere with the transmitted IR. The IR system is configured to detect a change in orientation.

The means for detecting the orientation 910 of the milk container may be configured to determine if the milk container is within a predefined range of allowed orientations. The milk container may be configured to vent the air only when the milk container is in the allowed orientations. For example, the allowed orientations may be where the user is upright or near upright. If the user is outside the predefined range of allowed orientations, there is a risk of milk exiting the milk container via the means for venting air.

In some embodiments, the actuator 906 may be configured to open the valve 904 to control the process of venting. The actuator 906 opens and closes the valve. Excess air held in the milk container is removed due to the diaphragm resetting to the level of the liquid in the bottle. When the dry side of the milk container is equalized to the atmosphere, the diaphragm provides a small positive pressure against the wet side. When the actuator 906 opens the valve 904, the small positive pressure is allowed to release.

This resets the diaphragm and removes excess air until the diaphragm is restricted by the liquid in the bottle. The diaphragm does not have enough spring force to displace the liquid, only air. That is, the diaphragm has a spring force low enough such that it will not displace liquid but high enough that it will displace excess air.

The actuator 906 may be a solenoid actuator. Of course, any suitable actuator may be used. When the actuator 906 closes the valve 904, no air or indeed liquid can flow out of the valve. When the valve 904 is closed the pressure in the milk container stays constant. The valve 904 may be described as an active valve.

Figure 10A:
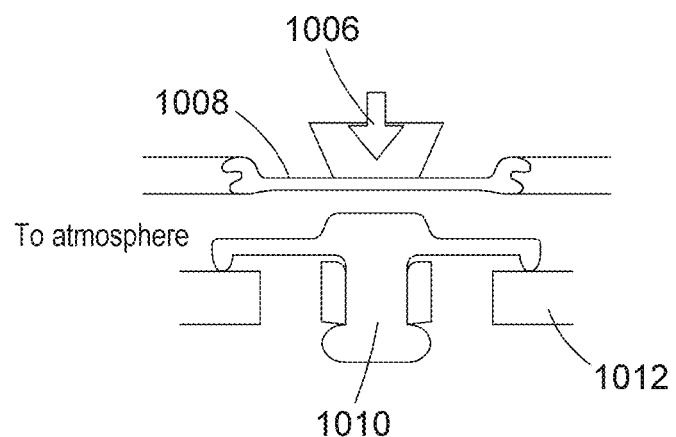
FIGS. 10A and 10B show a venting system according to an embodiment of the invention.
Figure 10B:
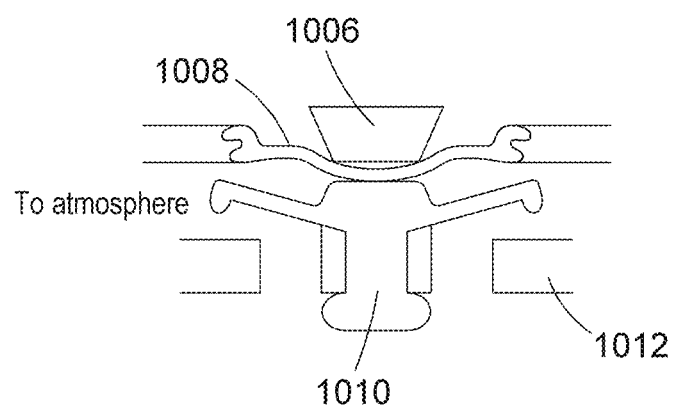

Reference will now be made to FIGS. 10A and 10B.

According to some embodiments, means for venting air comprising a valve located on the wet side of the container and an actuator configured to open the valve is depicted in FIGS. 10A and 10B.

The means for venting air may comprise: an actuator 1006, a flexible sealing portion 1008 and a valve portion 1010. FIG. 10A depicts the actuator 1006 at rest and the valve portion 1010 in the closed position. In the closed position, air is not being vented from the milk container. When the valve portion 1010 is closed, air cannot escape from the milk container. At rest, the actuator 1006 may be in contact with or in close proximity to the flexible sealing portion 1008.

FIG. 10B depicts the actuator 1006 in an engaged position which causes the valve portion 1010 to be in the open position. In the open position, air is vented from the milk container. When the actuator 1006 is engaged, the actuator 1006 makes contact with the flexible sealing portion 1008, flexing the flexible sealing portion 1008 and flexing the valve portion 1010. When flexed, the valve portion 1010 is open, allowing air to escape from the milk container. In the open position, air is vented from the milk container via an air channel between the flexible sealing portion 1008 and the milk container wall 1012. The air channel connects to the atmosphere external to the breast pump system.

Figure 11:
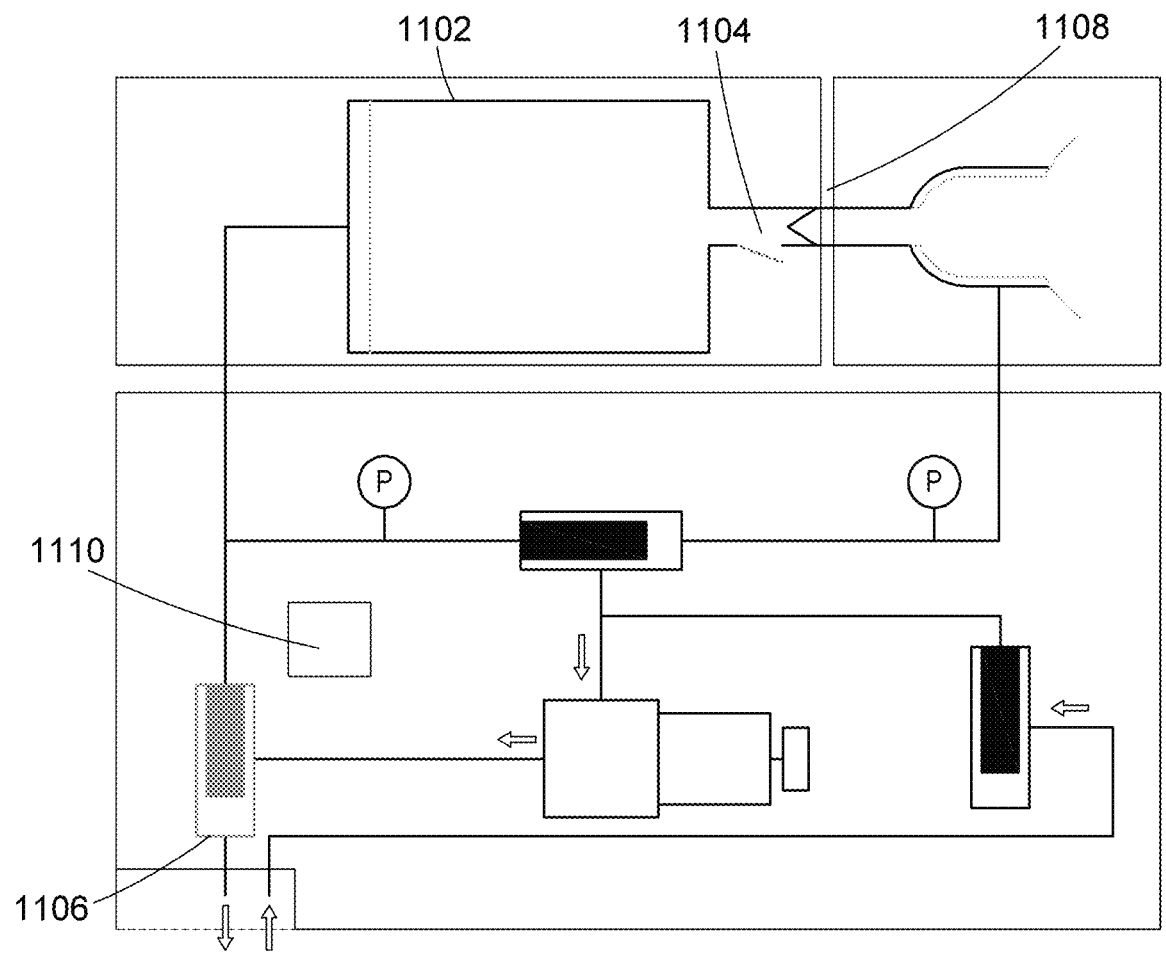
FIG. 11 shows a venting system according to an embodiment of the invention.

Reference will now be made to FIG. 11.

FIG. 11 depicts a milk container 1102 according to the some embodiments. The milk container 1102 may comprise means for venting air. The means for venting air may comprise a valve 1104 located on the wet side of the container and configured to open in response to air applied to the dry side of the container.

The breast pump system may also comprise a means for pressuring the milk container 1106. For example, the means for pressuring the milk container 1106 may be a solenoid. The means for pressuring the milk container 1106 may be a pump connected to the dry side of the milk container. The means for pressuring the milk container 1106 may be configured to increase the pressure on the dry side of the milk container. This causes the dry side to increase in volume, causing the wet side to decrease in volume and vent out air from the milk container and towards the non-return valve 1108. The vented air can escape through the valve 1104, such as a non-return valve, flap valve, membrane microvalve, ball microvalve, etc. The valve 1104 is a one-way valve which is configured to only allow vented air from the milk container to escape. The valve 1104 does not let atmospheric air enter the system.

In some embodiments, the milk container 1102 may comprise means for detecting the orientation 1110 of the milk container. The means for detecting the orientation 1110 of the milk container may operate in a similar way as described in relation to FIG. 8.

Figure 12:
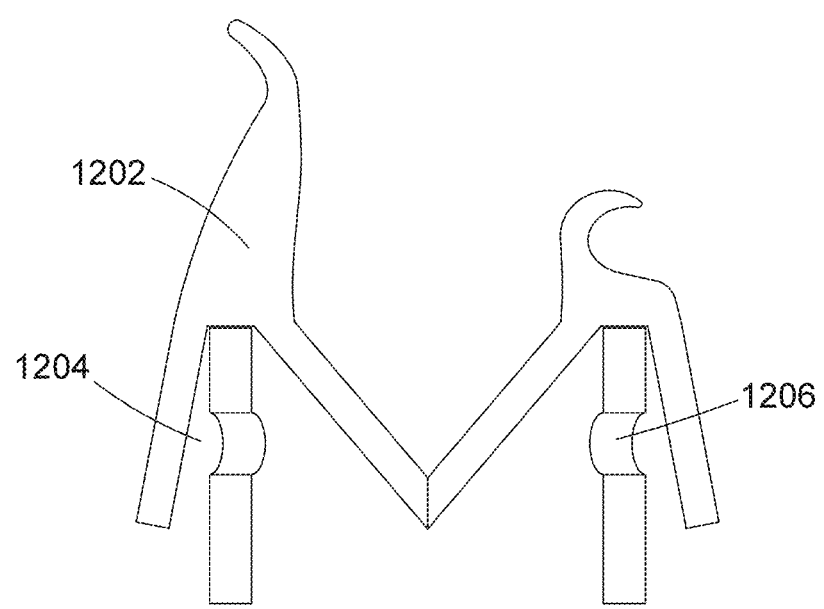
FIG. 12 shows a vent valve according to an embodiment of the invention.

Reference will now be made to FIG. 12.

In some examples, the valve 1104 located on the wet side of the container configured to open in response to air applied to the dry side of the container may be integrated into the non-return valve 1108. An example is depicted in FIG. 12. There is a first valve 1204 on one side of the wall of the nipple tunnel and a second valve 1206 on the opposite side of the nipple tunnel. The nipple tunnel may be defined as a channel between the milk container and the breast shield.

Figure 13:
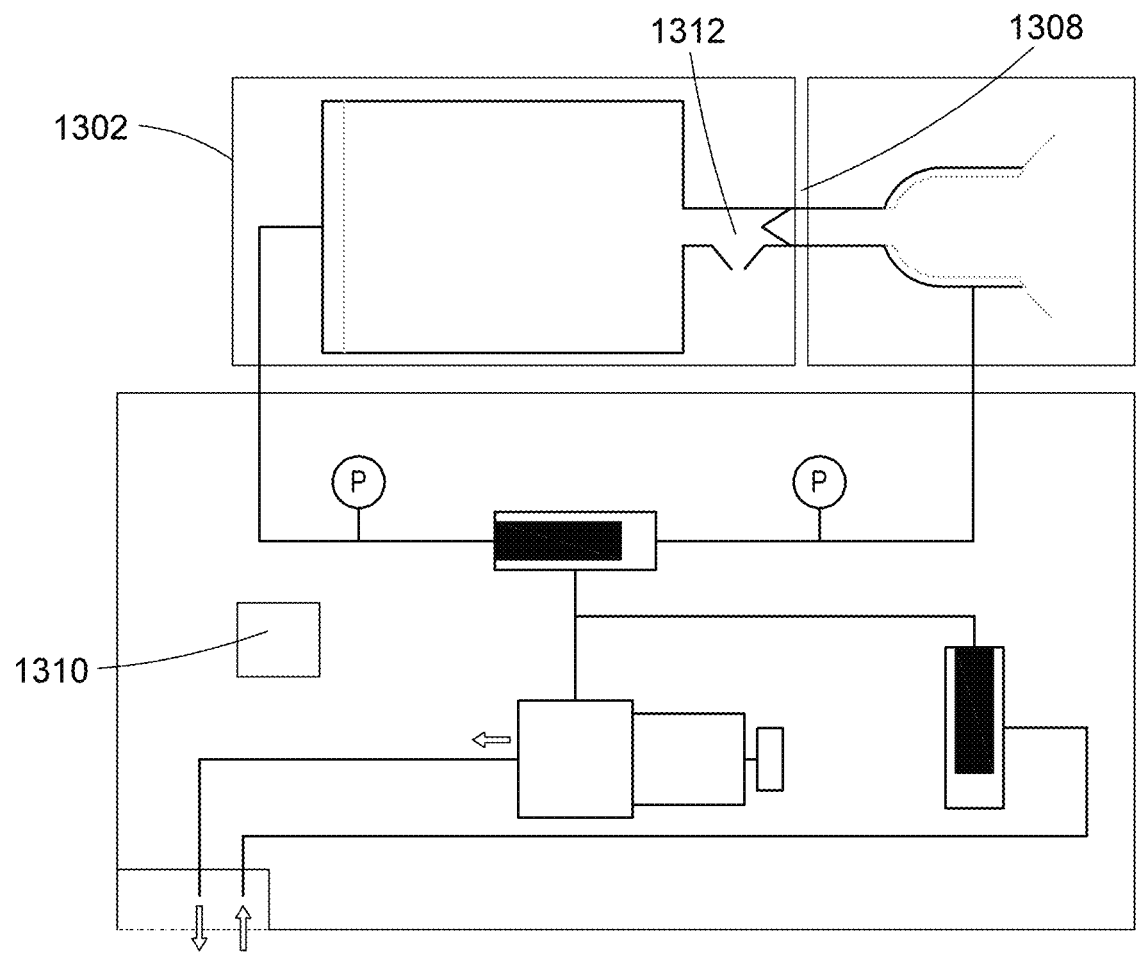
FIG. 13 shows a venting system according to an embodiment of the invention.

Reference will now be made to FIG. 13.

FIG. 13 depicts a milk container 1302 according to the some embodiments, wherein the means for venting air comprises a non-return valve 1312 located on the wet side of the container. The non-return valve 1312 may be described as the second non-return valve, an additional non-return valve to the first non-return valve 1308 which separates the milk container and breast shield. The non-return valve 1312 may be located on any suitable part of the wet side of the container.

The breast pump may be configured to pump the milk container 1302 to atmospheric pressure, such that excess air in the wet side is expelled via the non-return valve 1312. This configuration depicted in FIG. 13 is advantageous because it makes use of the breast pump's existing architecture without the need for additional components such as actuators or solenoids.

The non-return valve 1312 remains closed during a pumping phase of the operation of the breast pump. The non-return valve 1312 opens to expel excess air in the air venting phase of operation.

In some embodiments, the milk container 1302 may comprise means for detecting the orientation 1310 of the milk container. The means for detecting the orientation 1310 of the milk container may operate in a similar way as described in relation to FIG. 4. As described above, a milk-volume measurement process may measure the volume of milk and/or air in the milk container by changing the pressure or volume of the milk container. In one embodiment, the milk container 1302 may be configured to vent air from the non-return valve 1312 during the milk-volume measurement process. As the pressure or volume of the milk container changes, it may push out excess air which is expelled through the non-return valve 1312. This may occur every time the milk-volume measurement process is run.

Figure 14:
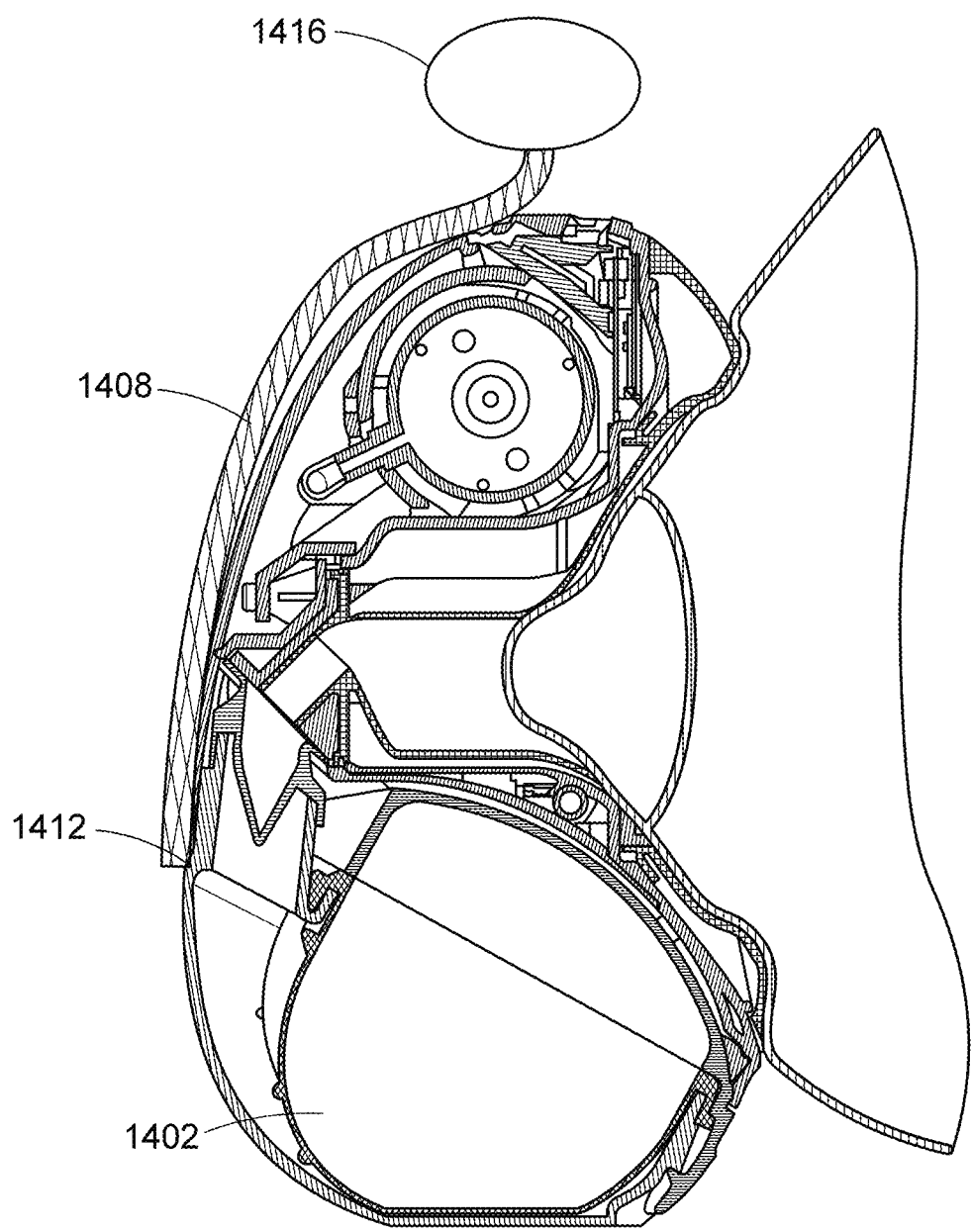
FIG. 14 shows a venting system according to an embodiment of the invention.

Reference will now be made to FIG. 14.

FIG. 14 depicts a milk container 1402 according to the some embodiments, wherein the means for venting air comprises an opening 1412 on the wet side, a tube 1408 connected to the opening, and a valve 1416 connected to the tube and located on an external side of the breast pump, wherein the valve is configured to be actuated by a user.

The valve 1416 may be configured to be user accessible. For example, the valve 1416 may be located on the topmost point of the breast pump milk container system for easy access.

This configuration allows the user to relieve air pressure/excess air whilst pumping. Advantageously, this configuration can also allow for a quick decant of milk for high volume milk producer users. To decant, the user would need to actuate the valve 1416 and move the orientation of the system such that the milk flows from the milk container 1402 and out of the valve. The valve 1416 may be any suitable valve.

The milk container described thus far may comprise a flexible diaphragm located inside the milk container. In some embodiments, the flexible diaphragm forms part of a wall of the milk container. The flexible diaphragm forming part of a wall of the milk container will now be described.

Figure 15A:
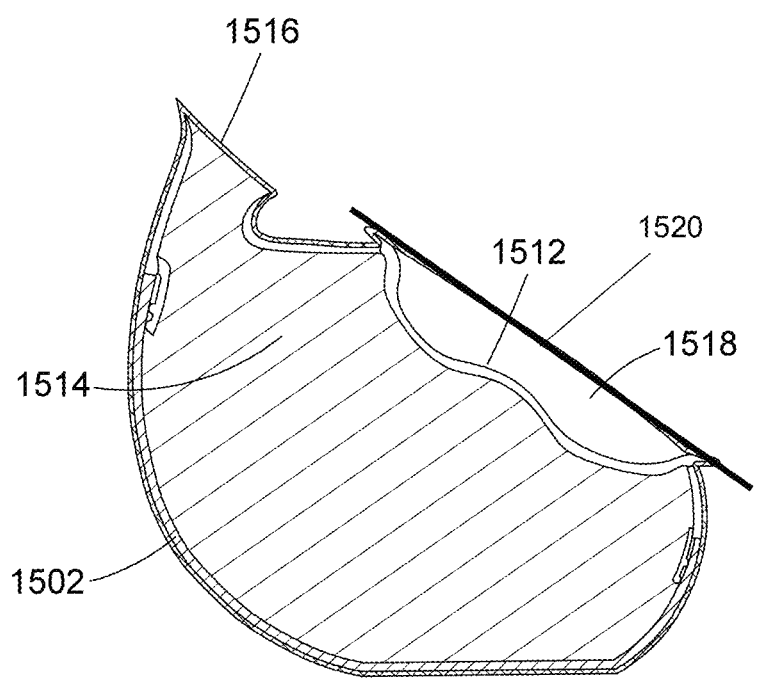
FIGS. 15A and 15B show a system according to an embodiment of the invention.
Figure 15B:
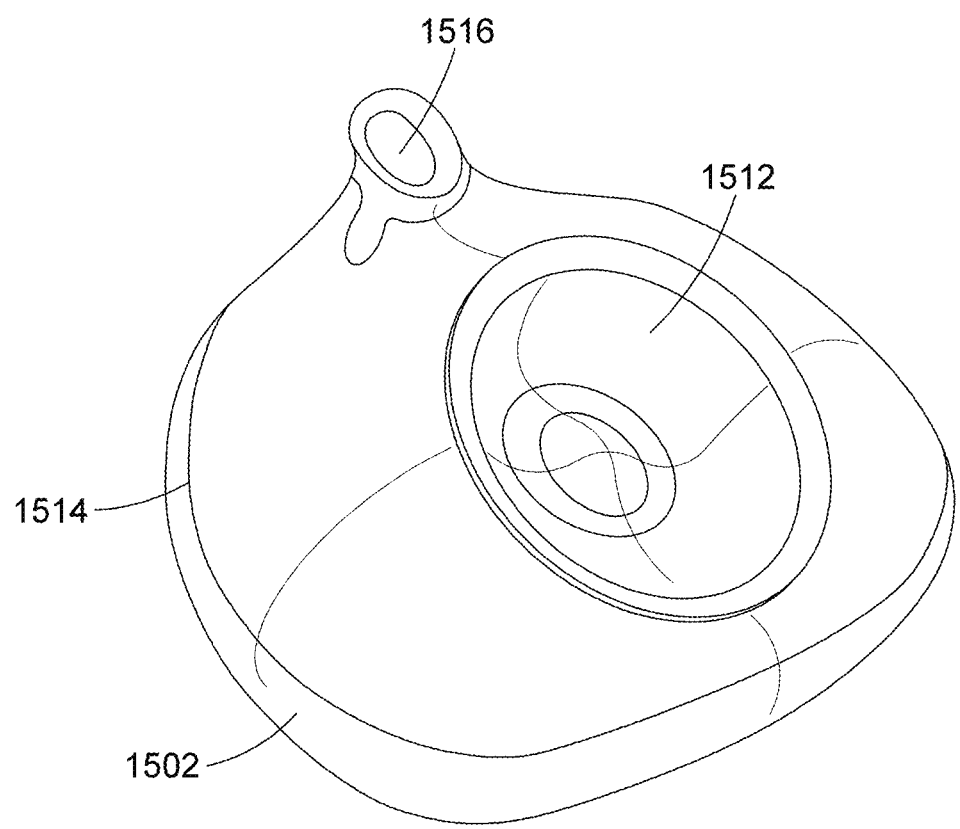

Reference will now be made to FIGS. 15A and 15B. FIG. 15A is a cross sectional view of a milk container 1502. FIG. 15B is a three dimensional view of the milk container 1502.

FIGS. 15A and 15B depict a milk container 1502 according to the present disclosure, wherein the flexible diaphragm forms part of a wall of the milk container. That is, the diaphragm forms part of an external wall of the milk container. In this embodiment, the "dry side" is external to the milk container and the "wet side" is internal to the milk container.

The flexible diaphragm is activated by an air pump applying negative pressure on the dry side of the diaphragm. In some examples, in a relaxed state the diaphragm has a non-flat profile, such as a curved or undulating profile. This enables the diaphragm to move without requiring the diaphragm material to stretch.

A milk container system is comprised of the milk container, the diaphragm forming part of the wall of the container, and an external portion which forms a chamber on the dry side of the diaphragm.

The wet side 1510 of the container is larger than the dry side 1518 of the container system. In FIG. 15A, the wet side 1514 is shown by the dashed area and the dry side 1518 as the non-dashed area. The dry side 1518 is not shown in FIG. 15B. The diaphragm 1512 may have a diameter smaller than the diameter of the milk container 1502. This configuration may be combined with any of the other embodiments described herein.

The diaphragm 1512 may form part of the exterior of the milk container 1502. That is, the diaphragm 1512 may form a wall of the milk container where one side of the diaphragm is internal to the milk container and the other side of the diaphragm is external to the milk container.

The diaphragm 1512 may be sealably attachable to the breast pump housing to form a dry chamber therebetween, defining the "dry side" of the diaphragm. An air pump pumps air into or from the dry chamber to engender movement in the diaphragm to create a suction in the milk container to draw breast milk into the milk container. The wet side and the dry side of the diaphragm in the embodiment in FIGS. 15A and 15B perform the same function as in the other embodiments disclosed herein, and therefore features of those embodiments apply to and can be combined with the embodiment in FIGS. 15A and 15B.

As described above, the breast pump may comprise a housing. A portion of the housing 1520 is illustrated in FIG. 15A. The diaphragm 1512 may be sealably attachable such that it forms a hermetic seal when attached to the housing. The diaphragm 1512 may be attachable such that it can be attached and unattached by the user. The dry chamber 1518 may be formed by the milk container and the housing. FIG. 15A shows the milk container 1502 attached to part of the housing 1520 such that the dry chamber 1518 is formed on the dry side of the diaphragm. FIG. 15B shows the milk container 1502 unattached to the housing such that no dry chamber is formed.

The milk container 1502 may meet the housing at a sealing lip, the sealing lip running circumferentially around the diaphragm. In some examples, the diaphragm comprises the sealing lip. In some examples, the milk container comprises the sealing lip on the wall which meets the diaphragm. The sealing lip may be configured to seal a flat surface 1520 of the housing to form the dry chamber 1518. In some examples, the housing of the breast pump has a flat surface 1520 for sealing to the milk container, such that one wall of the dry chamber is flat. In some examples, the housing has a curved section and a flat surface, where the flat surface abuts the sealing lip to form a seal. This creates a curved wall of the dry chamber 1518, which provide more room for the diaphragm to move into.

The diaphragm 1512 may be overmolded on the milk container to form the wet section 1514 inside the milk container, and the diaphragm sealably attached to the housing to form the dry chamber 1518.

As described above, the milk container 1502 may comprise the diaphragm 1512. The milk container may be removably attachable to the rest of the breast pump by a user. The diaphragm forms part of the milk container and is removably attachable from the breast pump with the other components of the milk container 1502, such that the user can empty milk from the container after a pumping session. The diaphragm 1512 may form part of a wall of the milk container 1502. In other words, the diaphragm 1512 may form part of the milk container surface. For example, the diaphragm 1512 may form around 50%, 30% or 10% of the milk container surface. Any suitable percentage of the milk container surface may be used.

The dry chamber 1518 may comprise a portion of the housing of the breast pump. That is the dry chamber 1518 may be part of the breast pump contained in the same housing as other components of the breast pump, for example, the air pump.

The milk container 1502 may comprise a first opening 1516 for receiving milk from the breast pump along a milk path. The first opening 1516 leads to the wet side. The milk path is similar to the milk path already described, for example the milk flows along the milk path through the breast shield and the nipple tunnel. The dry chamber 1518 may comprise a second opening for connection to an air pump. The second opening may be within the housing.

The first opening 1516 may be for pouring collected milk out of the milk container 1502. Alternatively, the milk container 1502 comprises a separate pouring opening for pouring collected milk out of the milk container.

The diaphragm forms part of the wall of the container. That is, the milk container, into which the milk flows from the milk path, is defined by a body forming walls around an internal chamber for collecting milk. The milk container is connectable to and removable from a milk path having a valve. Milk flows through a valve and into the milk container. The diaphragm forms a wall of the container and therefore is part of the body which is connectable to and removable from the milk path. In use, milk enters the milk container along a milk path, passing a valve before entering the milk container. The milk then collects in the milk container for the duration of the pumping session. The diaphragm forms part of the wall of the milk container. As milk collects in the container it touches the walls of the container. It may therefore fill up against the diaphragm.

The milk comprises an opening for receiving milk along a milk path and a main body for collecting milk. Milk is collected and stored in the main body during the pumping session. The diaphragm forms part of a wall of the main body of the milk container.

The diaphragm 1512 may be located on a portion of the milk container 1502 which, when the breast pump is positioned for use to receive milk from the user of the breast pump, forms a side or an upper portion of the milk container. FIG. 15A shows the breast pump positioned for use to receive milk from the user of the breast pump, this position can be considered upright. As shown in FIG. 15A, the diaphragm 1512 forms an upper portion of the milk container 1502.

In other embodiments, when the breast pump is positioned for use to receive milk from the user of the breast pump, the diaphragm forms a lower portion of the milk container. In these examples, the diaphragm may be configured to have enough spring force to overcome the pressure caused by the weight of the milk pressing down on the diaphragm.

The diaphragm 1512 may be located on the side of the milk container 1502 towards the user, when in its upright position. That is, the side of the milk container which is closer to the user's breast.

The milk container 1502 may have a flat bottom to allow the milk container to be stood on a surface. The diaphragm 1512 may form a side wall of the milk container, and may be on an upper portion of the milk container. That is, the diaphragm may be on a side wall on the upper half of the milk container. Alternatively, the diaphragm may form a top part of the milk container. In other embodiments, the diaphragm may be positioned elsewhere on the milk container.

The milk container 1502 may be a breast shaped hemispherical or half-ellipsoid shape, comprising a domed section and a flexible section. The domed section may be shaped to match or conform with the shape of a breast and/or bra. The shape of the milk container may be described as egg shaped or pebble shaped. The flexible section is the diaphragm 1512. The milk container 1502 may also comprise a substantially flat section at the bottom of the milk container such that the milk container can rest on a surface. In use, when worn by a user, the domed section may face outwards away from the user to conform with a bra. The bottom may be substantially flat, and the diaphragm may be positioned towards the user. The wall portion facing the user during use may be angled (i.e. not vertical).

In other examples, the diaphragm is located on other portions of the milk container. The diaphragm may be positioned in any conceivable location forming a portion of the wall of the main body of the milk container.

The milk container 1502 defines a main internal chamber, and the diaphragm 1512 forms part of the walls of the main internal chamber. That is, the diaphragm forms part of a wall of the main body of the milk container.

The milk container 1502 may comprise a rigid body and a hole, the hole sealed by the diaphragm 1512. Therefore, the walls of the milk container 1502 may comprise a rigid portion (the rigid body) and a flexible portion (the diaphragm 1512). The hole may be substantially the same shape and size as the diaphragm 1512. The hole may be hermetically sealed by the diaphragm 1512.

The diaphragm may be overmolded on the rigid portion of the container, or other forms of attaching the diaphragm to the rigid portions of the container may be used. The diaphragm 1512 may be substantially round, circle and/or oval shaped. The diaphragm 1512 may be a hemispherical bowl shape, a spherical dome and/or a spherical dome shape.

The diaphragm 1512 may be configured to be activated by low air pressure. The diaphragm 1512 may deform under low air pressure, transferring pressure from one side of the diaphragm to the other side. The diaphragm 1512 may oscillate it's position with air pump cycles as the pressure cycles from a higher pressure to a lower pressure.

FIG. 15A shows the milk container 1502 empty of milk. The wet side 1514 forms the entire inside of the milk container 1502. When the milk container 1502 is empty of milk, the wet side 1514 makes up the majority of the total volume of the milk container system while the dry chamber 1518 makes up a smaller volume of the milk container system. Due to the size of the wet side 1514 and the fact it makes up the entire milk container, there is a large amount of air in the wet side when the milk container 1502 is empty of milk.

When milk fills the milk container, the size of the wet side 1514 may increase due to an increased combined volume of air and milk. In turn, the dry side (aka the dry chamber 1518) may decrease in size. This happens by the diaphragm moving outwards from the wet side and into the dry side, hence decreasing the volume of the dry chamber and increasing the volume of the wet side.

Given there is air in the container (i.e. in the wet side) at the beginning of the pumping process, this air takes up internal volume which could otherwise be filled with milk. In order to reach maximum milk capacity of the milk container 1502, so that the container holds much milk as possible, air needs to be vented out of the wet side 1514 in order to make space for the milk. When at maximum capacity of milk, the total volume of the milk container 1502 will be substantially full of milk.

When milk fills the milk container, the size of the wet side 1514 may increase due to an increased volume of both air and milk. In turn, the dry side 1518 may decrease in size. In order to reach the maximum milk capacity of the milk container 1502, air needs to be vented out of the wet side 1514 in order to make space for the milk. When at maximum capacity of milk, the total volume of the milk container 1502 will be substantially full of milk. Air may be vented out according to any configuration and/or method described with reference to FIGS. 9 to 14. As described with reference to FIGS. 9 to 14, air may be vented multiple times throughout a pumping session.

Advantages

The non-return valves provided herein may have a small cracking pressure to overcome. This makes the milk container resilient to leaks even when there is no vacuum inside the container. This is useful, for example, when the pump is off but the bottle is full of milk and the vent valve is covered by milk. If there were no cracking pressure, just the weight of the milk would be enough for it to open and milk could leak out. If there is a cracking pressure, the valve will remain shut unless the pressure inside the bottle is greater than the cracking pressure.

Throughout the description it is described that air is vented out. However, more broadly, it is possible to vent out any positive pressure according to the present disclosure.

Milk Measurement

The milk measurement system described herein measures the air volume on both wet and dry side combined and subtracts this from the container volume to calculate the milk volume. Ideally, for venting it would be helpful to know the air volume contained on the wet side of the container only, as this may allow the system to vent air only when required.

When either milk or air enter the wet side of the container, the diaphragm is displaced and moves inside the bottle towards the dry side. The diaphragm's position is ultimately limited by the bottle or the rest of the breast pump device. When a quantity of milk or air has entered the wet side of the bottle to move the diaphragm to its most extreme position, such that the diaphragm can no longer move any further, the diaphragm can be considered to have reached its extreme of movement and "maximum" position. When the diaphragm has reached its maximum position, the air volume on the dry side of the bottle is 0 (or very close to 0).

The volume of fluid (air+milk) in the container is the sum of the volume of fluid on the wet side and the volume of fluid on the dry side. When the diaphragm has reached its maximum position and the dry side volume is zero, the total volume of fluid on the wet side (air+milk) is equal to the side of the container.

Therefore, when the diaphragm has reached its maximum position, the air volume on the wet side can be calculated as follows:

$$\text{Wet side air volume} = \text{Container size} - \text{milk measurement volume}$$

It is possible to detect the diaphragm topping out by monitoring the pressure (for example, via a pressure sensor) whilst pumping the bottle at the same time as running a milk measurement. Pumping the bottle may include, for example, creating a pumping vacuum and/or creating or maintaining a base level vacuum. When the diaphragm tops out, the rate of pressure change will dramatically increase. This is because the diaphragm's movement is now prevented (by the construction of the breast pump). In other words, when the milk has filled the wet side of the container, the milk pushes the diaphragm into its maximum position. The geometry of the breast pump means at some point the diaphragm will have no more space to move as the dry side approaches zero volume.

When the rate of change of pressure reaches a threshold value, the diaphragm can be considered to have reached its maximum position. Therefore, when the rate of change of pressure threshold is reached, the volume of liquid in the container as calculated in the milk volume measurement described herein is used to calculate the volume of air in the container by:

a. $\text{volume of air} = \text{container size} - \text{volume of liquid}$.

Then, the volume of air can be vented out of the milk container.

The means for venting air from the wet side of the container when connected to the breast pump may be configured to only vent air when the diaphragm has reached its maximum position and the calculated milk volume is less than the expected capacity of the milk container. The milk-volume measurement process is the process described herein for determining the amount of liquid in a container.

This improves efficiency of the system by only venting when it is necessary to do so. For example, a user who re-adjusts her breast pump multiple times during a pumping session increases the risk of air leaks and excess air entering the milk container. This user will have the milk vented more often to remove the excess air and allow for maximum capacity of milk to be collected in a single session.

The means for venting air from the wet side of the container may only vent air when the milk volume is below the expected milk capacity and the diaphragm has reached its maximum position.

As described above with reference to FIG. 11, one of the methods and systems to vent air from the wet side of the container was to use the air pump to push positively pressurised air into the dry side of the container. In FIG. 11, on the wet side of the milk container 1102 is a non-return valve 1104 configured to open when the pressure exceeds a pre-set value.

Figure 16:
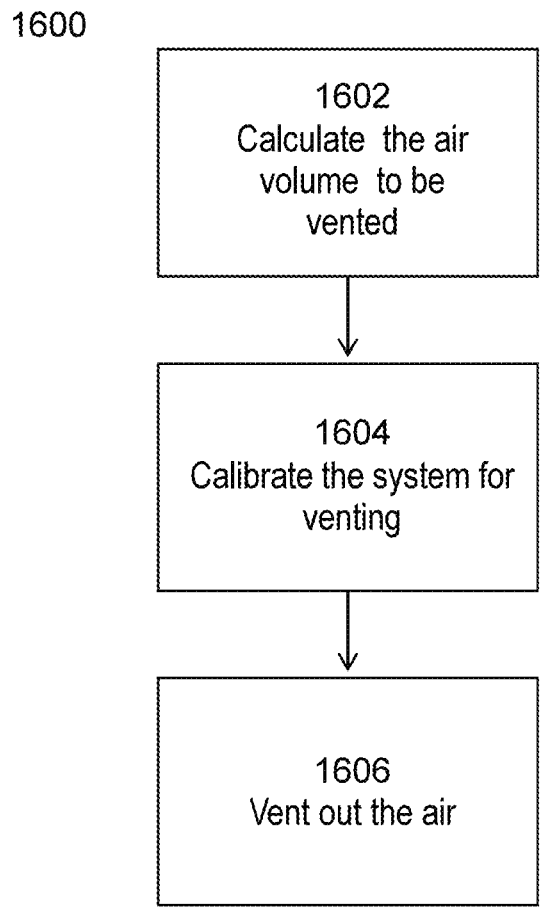
FIG. 16 shows a venting method according to an embodiment of the invention.

As mentioned above, air venting would start only when the diaphragm has reached its maximum position, for example indicated by a large spike in pressure in the system, and milk measurement volume indicates that the milk container is not full of milk. A method for venting the correct amount of air out of the milk container is described with reference to FIG. 16.

In some embodiments, a first step 1602 is to calculate the air volume to be vented out. The amount of air that needs to be vented out of the wet side of the container can be calculated with the equation:

Volume of air to be vented = Container size − milk measurement volume

The milk measurement volume is determined by processes described herein for determining the amount of liquid in a container. The container size is known from manufacture.

In some embodiments, a next step 1604 is to calibrate the system for venting. The calibration steps may be:

Connect an air flow rate meter to or near to the wet side of the container, after the non-return valve. For example, referring to FIG. 11, after the non-return valve 1004.

With the flexible diaphragm in its equilibrium starting position, and container empty of liquid, turn the pump on and measure the flow rate measurements vs the number of pump cycles. As described above, the number of pump cycles can be measured in a number of ways, for example using a linear or rotary encoder.

From the flow rate measurements and number of pump cycles, calculate the air volume pumped out for each pump cycle.

Use the maximum air volume pumped out for each pump cycle as the calibrated value for the volume of vented air. That is, the volume of vented air per pump cycle. The maximum value is used so that the system always underdoses air out of the wet side of the container. This is a mechanism to prevent too much air being vented and then squirting the milk contained within the container towards the user.

In some embodiments, a next step 1606 is to vent out the air. To vent out the air, the steps may be as follows:

1. Calculate the pump cycles required to vent out the volume of air calculated in step 1602. The following equation may be used:

$$\text{Pump cycles required} = \frac{\text{volume of air to be vented}}{\text{volume of vented air per pump cycle}}$$

The air to be vented is calculated at step 1602. The volume of vented air per pump cycle is calculated at step 1604.

2. Run the pump for the calculated number of pump cycles (e.g. encoder revolutions). As explained above, the solenoids are configured such that the positive pressure outlet of the pump is blowing into the container.

A second method for venting the correct amount of air out of the milk container will now be described. This method is similar to the calibration phase described with reference to FIG. 3.

The positive pressure pump may be connected to the milk container without the non-return valve for venting air. Then the pump increases pressure in the milk container to predetermined pressure target whilst recording synchronised pressure readings and pump cycle count (e.g. encoder revolutions).

Using similar steps as described in the calibration phase of FIG. 3, the air pumped in per pump cycle (e.g. encoder revolution) as a function of the dry side pressure can be calculated.

For each synchronised pressure reading and pump cycle count reading recorded (starting with synchronised readings from before reaching the target pressure), the following steps may be used:

1. Measure atmospheric pressure and, optionally, temperature of the container before pumping to the pressure target 2. Calculate moles of gas pumped into the container Moles Pumped into $$= \text{Moles of gas in volume}_{atmos} - \text{Moles of gas in volume}_{current\ threshold}$$

Where, using ideal gas law:

$$\text{Moles of gas in volume}_{atmos} = \frac{\text{atmospheric pressure} \times \text{volume of calibration volume}}{\text{molar gas constant} \times \text{temperature}}$$

$$\text{Moles of gas in volume}_{current\ threshold} = \frac{\text{current pressure} \times \text{volume of calibration volume}}{\text{molar gas constant} \times \text{temperature}}$$

3. Calculate volume pumped out of the container $$\text{Volume pumped in} = \frac{\text{moles pumped in} \times \text{molar gas constant} \times \text{temperature}}{\text{atmospheric pressure}}$$

4. Then calculate the difference between the number of pump cycles (e.g. encoder revolutions) of this sample vs the previous sample $$\text{Delta Pump Cycles} = \text{Pump cycles}_n - \text{Pump cycles}_{n-1}$$

5. Calculate the volume pumped in for this sample vs the previous sample $$\text{Delta Volume} = \text{Volume pumped in}_n - \text{Volume pumped in}_{n-1}$$

6. Calculate the volume pumped in per pump cycle for this sample $$\text{Volume pumped in per pump cycle} = \text{Delta volume}/\text{Delta pump cycles}$$

7. Derive an equation using regression analysis that calculates the volume pumped out per pump cycle from the current container pressure.

This derived equation may then used during air venting as follows:
1. Calculate the air required to be vented from the container size and milk measurement volume:

$$\text{Air to be vented} = \text{Container size} - \text{milk measurement volume}$$

As mentioned above, if too much air is vented out, it risks that milk will squirt out of the container also. This is wasteful and uncomfortable for the user. An additional mechanism to prevent milk squirting is provided.

Figure 17:
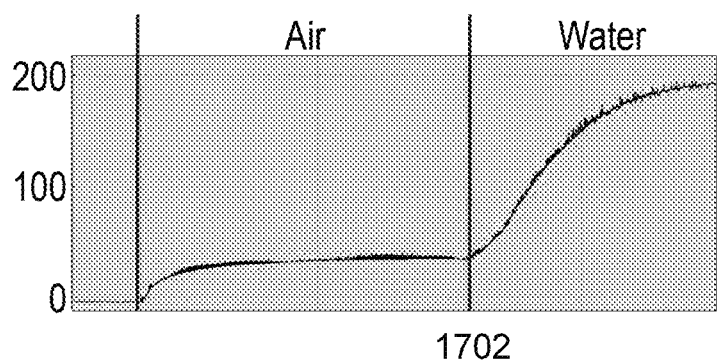
FIG. 17 shows an example graph to aid understanding in the present disclosure.

FIG. 17 shows a measured pressure (y axis) against time (x axis). This is the pressure near the non-return valve which is venting out the air. During measurement, the pump is positively pressurizing the milk container in order to vent air in the wet side out. At point 1702 of FIG. 17, the liquid has started to be vented out instead of the air, i.e. squirt has started. The graph shows that at 1702 when liquid passes through the non-return valve for venting, the back pressure detected by the milk container pressure sensor is significantly higher than when air passes through the valve. There is an inflection point in the graph at point 1702.

Therefore, by monitoring for a change in gradient of the pressure vs time (or pump cycles e.g. encoder ticks) curve, the inflection point can be identified and the pump turned off to prevent any extra liquid being squirted. Therefore, liquid coming out of the container can be stopped.

Features of the above embodiments can be combined in any suitable manner. It will be understood that the above description is of specific embodiments by way of aspect only and that many modifications and alterations will be within the skilled person's reach and are intended to be covered by the scope of the appendant claims.

The disclosure also includes the following clauses.
1. A method of measuring liquid volume in a sealed container of known volume comprising liquid and gas, the method comprising:
in a measurement phase measuring the volume of gas in the container by:
changing a first parameter of the gas by a known amount;
measuring a change in a second parameter of the gas; and
calculating the volume of gas in the container using the measured change and a predetermined operation equation; and
determining the volume of liquid in the container based on the calculation.
2. The method of clause 1, wherein the first and second parameter are each one of: the pressure, the amount of gas, the temperature and the volume of gas, and wherein the first parameter is different to the second parameter.
3 The method of any preceding clause wherein calculating the volume of gas in the container comprises:
using the measurement and a predetermined operation equation to determine the volume of air pumped from the container; and
using ideal gas law to calculate the volume of air in the container.
4. The method of any preceding clause wherein determining the volume of liquid in the container based on the calculation comprises:
calculating the difference between the volume of the container and the volume of air in the container.
5. The method according to any preceding clause wherein the predetermined operation equation is determined during a calibration phase.
6. The method according to any preceding clause wherein the calibration phase comprises, for a gas in a container, the gas having a known volume and pressure:
changing a first parameter by a threshold amount;
measuring a change in a second parameter; and
based on a relationship between the values, calculating an operation equation linking the change in the first value to the change in the second value.
7. The method according to any preceding clause, wherein the calibration phase comprises, for a plurality of containers of gas having a known volume and pressure:
changing a first parameter by a threshold amount;
measuring a change in a second parameter; and
performing a regression analysis on the measurements to calculate an operation equation.
8 The method of any preceding clause, wherein the first and second parameter are each one of: the pressure and the amount of gas.
9. The method according to any preceding clause, wherein changing the first parameter comprises pumping gas to or from the container using a pump.
10. The method according to clause 9, wherein changing a first parameter by a known amount comprises running a pump to a threshold value; and wherein measuring a change in a second parameter comprises measuring the pressure of the container, the amount of air pumped using an external flow rate sensor, the number of pump cycles, or the time taken to reach the threshold value.
11. The method of clause 7, wherein the threshold value is a threshold pressure in the container, a threshold volume of air pumped, a threshold time of operation of the pump, or a threshold number of pump cycles.
12. The method according to any preceding clause wherein the predetermined operation equation is determined during a calibration phase.
13. The method according to any preceding clause wherein the calibration phase comprises, for a gas in a container, the gas having a known volume and pressure:
running the pump to a threshold value;
measuring a change in the pressure or the number of pump cycles;
based on a relationship between the values, calculating an operation equation linking the change in the first value to the change in the second value.
14. The method according to any preceding clause, wherein the calibration phase comprises, for a plurality of containers of gas having a known volume and pressure:
changing a first parameter by a threshold amount;
measuring a change in a second parameter; and
performing a regression analysis on the measurements to calculate an operation equation.
15. The method according to clause 9, wherein the operation equation is derived from the change in pressure, the number of pump cycles and ideal gas law.
16. The method according to any preceding clause, wherein in the calibration phase the pump is run to a threshold value; and in the measurement phase, the pump is run to the same threshold value.
17. The method according to any preceding clause comprising:
in the calibration phrase, running pump to a threshold value for a number of containers of a different size.

18. The method according to clause 13, wherein deriving the operation equation comprises performing a regression analysis on collected data to determine a coefficient between the volume of air pumped and the change in pressure.
19. The method of clauses 1 to 6, wherein the one of the first and second values is volume of the gas and the other of the first and second values is one of pressure or temperate.
20. The method of clause 19 wherein changing a first parameter of the gas by a known amount comprises changing the volume of the container, and wherein; measuring a change in a second parameter of the gas comprises measuring a change in pressure or temperature.
21. The method of clauses 1 to 6, wherein changing a first parameter of the gas by a known amount comprises changing the volume of the container and changing the amount of gas, and wherein;
measuring a change in a second parameter of the gas comprises measuring a change in pressure.
22. The method of clause 21 wherein changing a first parameter of the gas by a known amount comprises connecting the container to a second container.
23. The method of clauses 1 to 6, wherein the first and second values are each one of pressure and amount of the gas.
24. The method of clause 23 wherein changing a first parameter of the gas by a known amount comprises increasing or decreasing the pressure in the container, and wherein;
measuring a change in a second parameter of the gas comprises measuring the time for gas to bleed from or into the container.
25. The method of clauses 1 to 6, wherein the first and second values are each one of pressure and volume of the gas.
26. The method of clause 25 wherein changing a first parameter of the gas by a known amount comprises adding liquid to the container, and wherein;
measuring a change in a second parameter of the gas comprises measuring the change in pressure in the container.
27. A measurement system comprising:
a pump configured to be attached to a container;
a pressure sensor for measuring the pressure in the container;
a processor configured to perform the method of any preceding clause.
28. The measurement system of clause 27 further comprising a sensor measuring the number of pump cycles or a flow sensor for measuring the volume of air pumped by the pump, wherein the pump is a negative pressure pump configured to pump air from the container, or wherein the pump is a positive pressure pump configured to pump air into the container.
29. The measurement system of clause 27 or 28, further comprising a container attached to the pump.
30. The measurement system of any of clause 27 to 29, wherein the measurement system is comprised in a breast pump for pumping milk from a user's breast into the container.
31. The measurement system of clause 30, wherein the pump is configured to create a pumping vacuum and a base level vacuum in the breast pump.
32. The measurement system of any of clause 30 or 31, wherein the pump is configured to measure the volume of fluid in the container between pumping cycles.
33. The measurement system of any of clause 27 to 29, wherein the measurement system is comprised in a negative pressure wound apparatus.
B1. A milk container for connection to a breast pump, comprising:
a first opening for receiving milk from the breast pump;
a second opening for connection to an air pump;
a flexible diaphragm located inside the milk container, wherein the first opening is located first side of the diaphragm defining a wet side of the container, and the second opening is located on a second side of the diaphragm defining a dry side of the container; and
means for venting air from the wet side of the container when connected to the breast pump.
B2. The milk container according to clause B1, wherein the means for venting air comprises a valve located on the wet side of the container and an actuator configured to open the valve.
B3. The milk container according to clause B1, wherein the means for venting air comprises a valve located on the wet side of the container configured to open in response to positive pressure applied to the dry side of the container.
B4. The milk container according to clause B1, wherein the means for venting air comprises a non-return valve located on the wet side of the container.
B5. The milk container according to clause B4, wherein the breast pump is configured to pump the milk container to above atmospheric pressure, such that excess air in the wet side is expelled via the non-return valve.
B6. The milk container according to clause B4 or clause B5, wherein the non-return valve remains closed during a pumping phase of the operation of the breast pump.
B7. The milk container according to clause B4, B5 or B6, wherein air is vented from the non-return valve during a milk-volume measurement process.
B8. The milk container according to any of clauses B1 to B7, wherein the wet side of the container is larger than the dry side of the container.
B9. The milk container according to clause B1, wherein the means for venting positive pressure comprises an opening on the wet side;
a tube connected to the opening; and
a valve connected to the tube and located on an external side of the breast pump, wherein the valve is configured to be actuated by a user.
B10. The milk container according to any of clauses B1 to B9, wherein the milk container comprises means for detecting the orientation of the milk container.
B11. The milk container according to clause B10, wherein the means for detecting the orientation of the milk container is configured to determine if the milk container is within a predefined range of allowed orientations and wherein the milk container is configured to vent the air only when the milk container is in the allowed orientations.
B12. The milk container according to any clauses B1 to B11, wherein the means for venting air from the wet side of the container when connected to the breast pump only vents air when a milk-volume measurement process determines:
the volume of the wet side of the milk container is approaching the maximum capacity of the milk container; and/or the excess air in the milk container is above a pre-defined threshold.

B13. The method according to B12, wherein when a rate of change of pressure threshold measured inside the container is reached, the volume of liquid in the container is used to calculate the volume of air in the container by:

$$\text{volume of air} = \text{container size} - \text{volume of liquid}.$$

The invention claimed is:

1. A method of measuring liquid volume in a sealed container of a breast pump of known volume comprising liquid and gas, the method comprising:
in a measurement phase, measuring the volume of gas in the container by:
changing a first parameter of the gas by a known amount by pumping gas to or from the container using a pump;
measuring a change in a second parameter of the gas; and
calculating the volume of gas in the container using the measured change and a predetermined operation equation derived from the change in pressure, the number of pump cycles, and ideal gas law;
determining the volume of liquid in the container based on the calculation.

2. The method of claim 1, wherein the first and second parameter are each one of: the pressure, the amount of gas, the temperature, and the volume of gas, and wherein the first parameter is different to the second parameter.

3. The method of claim 1, wherein calculating the volume of gas in the container comprises:
using the measured change and the predetermined operation equation to determine the volume of gas pumped from the container; and
using ideal gas law to calculate the volume of gas in the container.

4. The method of claim 1, wherein determining the volume of liquid in the container based on the calculation comprises:
calculating the difference between the volume of the container and the volume of gas in the container.

5. The method of claim 1, wherein the predetermined operation equation is determined during a calibration phase.

6. The method of claim 5, wherein the calibration phase comprises, for a gas in a container, the gas having a known volume and pressure:
changing a first parameter by a threshold amount;
measuring a change in a second parameter; and
based on a relationship between the values, calculating a second operation equation linking the change in the first value to the change in the second value.

7. The method of claim 5, wherein the calibration phase comprises, for a plurality of containers of gas having a known volume and pressure:
changing a first parameter by a threshold amount;
measuring a change in a second parameter; and
performing a regression analysis on the measurements to calculate an operation equation.

8. The method of claim 5, wherein the calibration phase comprises, for a gas in a container, the gas having a known volume and pressure:
running the pump to a threshold value;
measuring a change in the pressure or the number of pump cycles; and
based on a relationship between the values, calculating a second operation equation linking the change in the first value to the change in the second value.

9. The method of claim 1, wherein changing the first parameter by a known amount comprises running a pump to a threshold value, and wherein measuring a change in a second parameter comprises measuring the pressure of the container, the amount of gas pumped using an external flow rate sensor, the number of pump cycles, or the time taken to reach the threshold value.

10. The method of claim 7, wherein the threshold amount is a threshold pressure in the container, a threshold volume of gas pumped, a threshold time of operation of the pump, or a threshold number of pump cycles.

11. The method of claim 5, wherein in the calibration phase the pump is run to a threshold value, and wherein in the measurement phase, the pump is run to the same threshold value.

12. The method of claim 5, further comprising:
in the calibration phase, running the pump to a threshold value for a number of containers of different sizes.

13. The method of claim 1, wherein the operation equation is derived from performing a regression analysis on collected data to determine equation coefficients between the volume of gas pumped and the change in pressure.

14. The method of claim 1, wherein changing the first parameter of the gas by a known amount comprises changing the volume of the container, and
wherein measuring a change in a second parameter of the gas comprises measuring a change in pressure or temperature.

15. The method of claim 1, wherein changing the first parameter of the gas by a known amount comprises changing the volume of the container and changing the amount of gas, and
wherein measuring a change in a second parameter of the gas comprises measuring a change in pressure.

16. The method of claim 15, wherein changing the first parameter of the gas by a known amount comprises connecting the container to a second container.

17. The method of claim 1, wherein the first and second parameters are each one of pressure and amount of the gas, wherein changing the first parameter of the gas by a known amount comprises increasing or decreasing the pressure in the container, and
wherein measuring a change in a second parameter of the gas comprises measuring the time for gas to bleed from or into the container.

18. The method of claim 1, wherein the first and second parameters are each one of pressure and volume of the gas, wherein changing the first parameter of the gas by a known amount comprises adding liquid to the container, and
wherein measuring a change in a second parameter of the gas comprises measuring the change in pressure in the container.

19. The method of claim 10, wherein the threshold pressure is an altitude compensated threshold pressure.

20. The method of claim 19, wherein the altitude compensated threshold pressure is calculated by a method comprising:
calculating a pressure ratio;
measuring atmospheric pressure; and
calculating the altitude compensated threshold pressure.

21. The method of claim 1, wherein the volume of liquid in the container is used to calculate the volume of air in the container, and wherein the volume of air in the container is vented out of the container.

22. The method of claim 21, wherein when a rate of change of pressure threshold measured inside the container is reached, the volume of liquid in the container is used to calculate the volume of air in the container by:

volume of air=container size−volume of liquid.

23. A measurement system for a breast pump for pumping milk from a user's breast into a container, the measurement system comprising:
- a pump configured to be attached to a container and configured to create a pumping vacuum and a base level vacuum in the breast pump;
- a pressure sensor for measuring the pressure in the container; and
- a processor configured to perform a method of measuring liquid volume in the container of the breast pump of known volume comprising liquid and gas, the method comprising:
    - in a measurement phase, measuring the volume of gas in the container by:
        - changing a first parameter of the gas by a known amount;
        - measuring a change in a second parameter of the gas; and
        - calculating the volume of gas in the container using the measured change and a predetermined operation equation; and
    - determining a volume of liquid in the container based on the calculation.

24. The measurement system of claim 23, further comprising a sensor measuring a number of pump cycles or a flow sensor for measuring a volume of gas pumped by the pump, wherein the pump is a negative pressure pump configured to pump gas from the container, or wherein the pump is a positive pressure pump configured to pump gas into the container.

25. The measurement system of claim 23, further comprising the container attached to the pump.

26. The measurement system of claim 23, wherein the pump is configured to measure the volume of liquid in the container between pumping cycles.

27. The measurement system of claim 23, further comprising means for venting air from a wet side of the container.

28. A measurement system for a breast pump for pumping milk from a user's breast into a container, the measurement system comprising:
- a pump configured to be attached to a container;
- a pressure sensor for measuring the pressure in the container;
- means for venting air from a wet side of the container; and
- a processor configured to perform a method of measuring liquid volume in the container of the breast pump of known volume comprising liquid and gas, the method comprising:
    - in a measurement phase, measuring the volume of gas in the container by:
        - changing a first parameter of the gas by a known amount;
        - measuring a change in a second parameter of the gas; and
        - calculating the volume of gas in the container using the measured change and a predetermined operation equation; and
    - determining the volume of liquid in the container based on the calculation.

29. The measurement system of claim 28, further comprising a sensor measuring a number of pump cycles or a flow sensor for measuring a volume of gas pumped by the pump, wherein the pump is a negative pressure pump configured to pump gas from the container, or wherein the pump is a positive pressure pump configured to pump gas into the container.

30. The measurement system of claim 28, wherein the pump is configured to create a pumping vacuum and a base level vacuum in the breast pump.

* * * * *